US009040667B2

(12) United States Patent
Liao et al.

(10) Patent No.: US 9,040,667 B2
(45) Date of Patent: May 26, 2015

(54) ANTIBODY COCKTAIL

(75) Inventors: Zhiming Liao, Ventura, CA (US); Jeanette Musser, Ventura, CA (US)

(73) Assignee: Dako Denmark A/S, Glostrup (DK)

( * ) Notice: Subject to any disclaimer, the term of this patent is extended or adjusted under 35 U.S.C. 154(b) by 48 days.

(21) Appl. No.: 13/318,215

(22) PCT Filed: Apr. 27, 2010

(86) PCT No.: PCT/DK2010/000057
§ 371 (c)(1),
(2), (4) Date: Nov. 30, 2011

(87) PCT Pub. No.: WO2010/124689
PCT Pub. Date: Nov. 4, 2010

(65) Prior Publication Data
US 2012/0082999 A1    Apr. 5, 2012

Related U.S. Application Data

(60) Provisional application No. 61/174,623, filed on May 1, 2009.

(51) Int. Cl.
*C07K 16/00* (2006.01)
*G01N 33/574* (2006.01)

(52) U.S. Cl.
CPC ...... *G01N 33/57434* (2013.01); *G01N 2800/52* (2013.01)

(58) Field of Classification Search
CPC combination set(s) only.
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,149 A | 12/1982 | Bargiotti et al. | |
| 4,366,241 A | 12/1982 | Tom et al. | |
| 4,816,576 A | 3/1989 | Buysch et al. | |
| 5,744,585 A * | 4/1998 | Medenica et al. | 530/388.15 |
| 2005/0186642 A1 | 8/2005 | Tacha | |

FOREIGN PATENT DOCUMENTS

WO    WO 03/012067 A2    2/2003
WO    WO 2010/028646 A1    3/2010

OTHER PUBLICATIONS

Herawi et al (Am J Sur Path 31:889-894, 2007, abstract.*
Hameed et al, Semi in Diag Path 22:88-104, 2005, abstract.*
NordiQc online publication, Assessment Run 26, updated Mar. 7, 2009.*
Leong Ng et al (AAm J Clin Pathol 127:248-253, 2007.*
Kaurmann et al (Am J Clin Path 116:823-830, 2001.*
Better et al. "*Escherichia coli* Secretion of an Active Chimeric Antibody Fragment" *Science* 240(4855):1041-1043 (1988).
Bird et al. "Single-chain antigen-binding proteins" *Science* 242(4877):423-426 (1988).
Burford et al. "Effect of Storage on p63 Immunohistochemistry. A Time-course Study" *Appl. Immunohistochem. Mol. Morphol.* 17(1):68-71 (2009).
Chu et al. "Expression of Cytokeratin 5/6 in Epithelial Neoplasms: An Immunohistochemical Study of 509 Cases" *Mod. Pathol.* 15(1):6-10 (2002).
Cole et al. "Human monoclonal antibodies" *Mol. Cell. Biochem.* 62:109-120 (1984).
Cote et al. "Generation of human monoclonal antibodies reactive with cellular antigens" *Proc. Natl. Acad. Sci. USA* 80:2026-2030 (1983).
Engvall "Enzyme Immunoassay ELISA and EMIT" *Meth. Enzymol.* 70:419-439 (1980).
Hameed et al. "Immunohistochemistry in diagnostic surgical pathology of the prostate" *Semin. Diagn. Pathol.* 22:88-104 (2005).
Herawi et al. "Immunohistochemical antibody cocktail staining (p63/HMWCK/AMACR) of ductal adenocarcinoma and Gleason pattern 4 cribriform and noncribriform acinar adenocarcinomas of the prostate" *Am. J. Surg. Pathol.* 31(6):889-894 (2007).
Huston et al. "Protein engineering f antibody binding sites: Recovery of specific activity in an anti-digoxin single-chain Fv analogue produced in *Escherichia coli*" *Proc. Natl. Acad. Sci. USA* 85:5879-5883 (1988).
Jiang et al. "P504S. A New Molecular Marker for the Detection of Prostate Carcinoma" *Am. J. Surg. Pathol.* 25(11):1397-1404 (2001).
Köhler et al. "Continuous cultures of fused cells secreting antibody of predefined specificity" *Nature* 256(5517):495-497 (1975).
Kozbor et al. "Specific Immunoglobulin Production and Enhanced Tumorigenicity Following Ascites Growth of Human Hybridomas" *J. Immunol. Meth.* 81:31-42 (1985).
Molinié et al. "Diagnostic utility of a p63/α-methyl-CoA-racemase (p504s) cocktail in atypical foci in the prostate" *Mod. Pathol.* 17:1180-1190 (2004).
Molinié et al. "New markers in prostate biopsies" *Actas Urologicas Españolas* 31(9):1009-1024 (2007).
Moll et al. "The Catalog of Human Cytokeratins: Patterns of Expression in Normal Epithelia, Tumors and Cultured Cells" *Cell* 31:11-24 (1982).
Orlandi et al. "Cloning immunoglobulin variable domains for expression by the polymerase chain reaction" *Proc. Natl. Acad. Sci. USA* 86:3833-3837 (1989).

(Continued)

*Primary Examiner* — Lei Yao
(74) *Attorney, Agent, or Firm* — Finnegan, Henderson, Farabow, Garrett & Dunner, L.L.P.

(57) ABSTRACT

The present invention relates to a composition comprising at least three primary antibodies or fragments thereof, wherein the at least three antibodies or fragments thereof binds specifically to at least three different proteins, and wherein the at least three different proteins are AMCAR, CK 5/6, and HMWC. Methods for using the composition in diagnosis, prognosis, and assessing efficacy of treatment is further included as well as kits comprising said composition, and optionally, instructions of its use.

18 Claims, 7 Drawing Sheets

(56) References Cited

OTHER PUBLICATIONS

Sanderson et al. "An Analysis of the p63/α-Methylacyl Coenzyme A Racemase Immunohistochemical Cocktail Stain in Prostate Needle Biopsy Specimens and Tissue Microarrays" *Am. J. Clin. Pathol.* 121:220-225 (2004).

Signoretti et al. "*Ip63* Is a Prostate Basal Cell Marker and Is Required for Prostate Development" *Am. J. Pathol.* 157(6):1769-1775 (2000).

Skerra et al. "Assembly of a Functional Immunoglobulin $F_v$ Fragment in *Escherichia coil*" *Science* 240:1038-1041 (1988).

Srigley "Benign mimickers of prostatic adenocarcinoma" *Mod. Pathol.* 17:328-348 (2004).

Ward et al. "Binding activities of a repertoire of single immunoglobulin variable domains secreted from *Escherichia coli*" *Nature* 341:544-546 (1989).

Winter et al. "Man-made antibodies" *Nature* 349:293-299 (1991).

Yang et al. "Rare Expression of High-Molecular-Weight Cytokeratin in Adenocarcinoma of the Prostate Gland: A Study of 100 Cases of Metastatic and Locally Advanced Prostate Cancer" *Am. J. Surg. Pathol.* 23(2):147-152 (1999).

* cited by examiner

ANTIBODY COCKTAIL

CROSS-REFERENCE TO RELATED APPLICATIONS

This application is a U.S. national stage entry under 35 U.S.C. §371 of International Application Number PCT/DK2010/000057, filed Apr. 27, 2010, which claims priority to U.S. Provisional Application No. 61/174,623, filed May 1, 2009, both of which are incorporated herein by reference.

TECHNICAL FIELD

The present invention relates to the filed of prostate cancer. Particularly, it relates to a composition for an improved detection of prostate cancer, prostatic intraepithelial neoplasia (PIN), or benign mimics of prostate cancer, methods and uses thereof to detect prostate cancer, as well as its diagnostic and/or prognostic uses.

BACKGROUND OF THE INVENTION

Prostate cancer is one of the most common malignant diseases for which health-care intervention is sought worldwide. In many developed countries it is the most common non-cutaneous malignant disease. In US only, estimated new cases 2008 are about 186,320, and the death rate estimated to be about 28,660 for 2008 (US National Cancer Institute, estimated statistics for Prostate cancer, www.cancer.gov/cancertopics/types/prostate).

Men with prostate cancer have mostly no symptoms at all, especially in the early stages. Some symptoms that may indicate prostate cancer include difficult and painful urination, frequent urination, incomplete emptying of the bladder, decrease force of urine stream, blood in the urine, hip and back pain. When the cancer has spread to other parts of the body, symptoms may include bone pain, weight loss, anemia, kidney failure, weakness or paralysis caused by the spinal cord.

There are many types of prostate cancer and it is often present in many different parts of the prostate. The precursor to prostate cancer is known as prostatic intraepithelial neoplasia (PIN), this is also found in many different locations within the prostate.

Although there are many different kinds of prostate cancer the vast majority (around 95%) are of the type known as adenocarcinoma. As this is the most wide spread from it has become synonymous with the term prostate cancer.

The current preferred method for diagnosing early prostate cancer is prostatic needle biopsy since it has a low morbidity and provides specific information on the grade and extent of the tumour.

The most common site of origin of prostate cancer is in the peripheral zone (the main glandular zone of the prostate). The term adenocarcinoma originates from Adeno meaning 'pertaining to a gland', whilst Carcinoma relates to a cancer that develops in epithelial cells.

Available markers for diagnosing prostate cancer are inferior and the markers available have serious limitations relating to specificity. This results in less objective results by attribution or assignment bias which limits the accuracy of the resulting information.

Prostate-specific antigen, PSA, is still the main diagnostic tool despite its serious limitations, while studies of new markers are being performed and reported continuously.

PSA is a protein produced by both normal and cancerous prostate cells. A high level of PSA can be a sign of cancer, but the PSA level can also be raised in prostate conditions that are not cancer, i.e. they are benign, or if you have an infection. PSA is analyzed in blood samples. Since it affects the conclusion(s) drawn from the measured levels, one wants to rule out infections like e.g. a urine infection before carrying out a test.

Further, there is no PSA reading that is considered 'normal'. The reading varies from man to man and the normal level increases as you get older. As a rule of thumb, the higher the level of PSA, the more likely it is to be cancer. Sometimes a cancer may be diagnosed in a man with a 'normal' PSA reading. But usually, the higher the reading, the more likely it is to be cancer. There is thus a high uncertainty and certainly an attribution of subjectivity in diagnosing prostate cancer using PSA.

New studies emerging for other markers useful for diagnosing prostatic cancer are still subjected to attribution or assignment bias (depending on the pathologists experience and awareness) with more or less arbitrary chosen cut-off values used as standard values to decide the outcome of the decisive test where an assumption is made that no cancers are present below that cut of. The assumption may thus leading to wrong findings and, subsequently, wrong diagnosis for the patient.

US 2005/0186642 provides regents with primary antibodies and a detection system using antibody cocktails. Antibody cocktails are exemplified in the application with compositions comprising antibodies binding to i) high-molecular weight cytokeratin (HMWCK) (mouse antibody)+medium weight cytokeratin MWCK (rat antibody), and a composition comprising antibodies binding to ii) α-metyhylacyl-CoA-racemase (AMCAR) (rat antibody)+HMWCK+p63 (both mouse antibodies) (PIN cocktail).

Schuyler et al (Am. J. Clin. Pathol. 2004, 121:220-225) provides an antibody cocktail with antibodies binding to p63 and AMCAR in evaluation of prostate biopsy specimens (a PIN cocktail).

Molinié et al. (Modern Pathology, 2004, 17, 1180-1190) provides staining and evaluation of prostate specimen from surgical pathological files using antibodies binding to high molecular weight CK 5/6 or a cocktail with antibodies binding to p63 and AMCAR (AMCAR/p63, PIN cocktail).

Srigley, J., (Modern pathology, 2004, 17:328-348) provides immunohistochemical markers for benign mimickers of prostatic adenocarcinoma in diagnosis, and problems related thereto. Antibodies binding to HMWCK, cytokeratin 5 and 6 (CK5/6) and p63 are mentioned as basal cell markers and AMCAR/p63 is used as a PIN cocktail.

p63 is a nuclear protein selectively expressed in the basal cell compartment of a variety of epithelial cells. Normal prostate glands show selective p63 nuclear expression in basal cells and p63 is consistently undetectable in prostate cancer (Signoretti et al., 2000, Am. J. Pathol., Vol. 157, pg. 1768-1775). Antibodies raised to p63 thus give nuclear staining.

Nuclear staining is attributed to some inherent technical problems giving rise to an inconsistency and even lack of repeatability due to technical reasons. The fixation and permeabilisation steps always affect the availability of a proteins (i.e. the specific antigen) and thus, nuclear staining are more dependent thereon than cell-surface or cytoplasmic proteins due to the permeabilisation of the nuclear envelope. Further, even and exact cuttings as such as well as thickness thereof and spatial localisation of the cut in relation to the orientation of the cell also affect the availability of nuclear proteins, such as p63, to a higher degree than for cell-surface or cytoplasmic proteins. Also, a dividing cell may give rise to a diffuse staining—if any—compared to a non-dividing cell.

Further to be mentioned is that p63 is expressed in most, but not all, basal cells surrounding the prostate glands which further gives a degree of uncertainty when analysing staining of normal and possible prostate cancer tissue samples (Signoretti et al., 2000, Am. J. Pathol., Vol. 157, pg. 1768-1775).

Further, it is known in the art that stainings of the p63 antigen is sensitive to storage over time and a time course study has shown a progressive decline in the p63 intensity score with time (Effect of Storage on p63 Immunohistochemistry: A Time-course Study. *Appl Immunohistochem Mol Morphol.* 2009 January; 17(1):68-71).

Inconsistency in staining of the nuclear protein p63 will, of course, affect the conclusions drawn from the detection of this protein in the samples analysed. Thus, affecting the conclusions, even leading to a wrong conclusion, will affect the further diagnosis or prognosis of the patient and even the future care, treatment and even outcome of the individual. A wrong diagnosis or prognosis is thus highly un-appreciated both by patient and the hospital care system.

It is thus highly desirable to have a more reliable, but still, an equally easy detection of prostate cancer that further avoids the use of staining nuclear proteins such as e.g. p63 frequently used in new studies emerging on antibody-cocktails for detection and diagnosing of prostate cancer.

There is thus an urgent need to find better diagnostic and prognostic markers, means and methods when diagnosing and prognosing prostatic cancer in a simple and reliable way, as well as less biased means to perform an accurate and less biased method or assay for detecting prostatic cancer. Accordingly, the present invention seeks to provide means and methods to perform accurate and less biased diagnostic assays, in a simple and efficient way for routine testing when diagnosing or prognosing prostatic cancer.

SUMMARY OF THE INVENTION

One aspect of the present invention provides a composition comprising at least three primary antibodies or fragments thereof, wherein the at least three antibodies or fragments thereof binds specifically to at least three different proteins, and wherein the at least three different proteins are α-metyhylacyl-CoA-racemase (AMCAR), Cytokeratin 5 and 6 (CK5/6), and high-molecular weight cytokeratin (HMWCK).

P504S is a gene encoding for protein identified as α-metyhylacyl-CoA-racemase (AMACR) and is located in mitochondria and peroxisomes. As such, antibodies raised to this protein show cytoplasmic reactivity. A number of investigators have shown that antibodies to this over expressed protein are useful in recognition of prostate carcinoma (Jiang Z et al., *Am J Surg Pathol* 5 (11): 1397-1404, 2002).

Cytokeratin 5 and 6 (CK5/6) are intermediate-sized basic keratins. In normal tissue, CK5/6 are mainly expressed in keratinizing (epidermis) and nonkeratinizing (mucosa) squamous epithelium, as well as in basal-myoepithelial cell layer of the prostate, breast, and salivary glands. CK5/6 is down regulated in prostatic cancer. CK5/6 is a marker of basal cells which are fewer in cancer compared to normal prostate (Peiguo et al., Mod. Pathol., 2002, 15:6-10).

Cytokeratins 1, 5, 10 and 14 recognizable by mouse monoclonal antibody clone 34βE12 generally termed "high molecular weight cytokeratin" (abbreviated as HMWCK) are expressed on basal cells and. Prostate carcinoma has been reported to lack expression of HMWCK, however, reports on expression immunopositivity for HMWCK in metastatic prostate cancer have however shown that the cells do not have morphology of basal cells (Yang et al., 1999, 23:147-152). (for the purpose of discussion 34βE12 antibody, identifying CK1, CK5, CK10, and CK14, is herein interchangeably referred to as high molecular weight cytokeratin or HMWCK)

A further aspect of the present invention provides method for detecting in vitro AMCAR, CK 5/6, and HMWCK, the method comprising the steps of a) contacting said sample with a composition comprising at least three different primary antibodies or fragments thereof, wherein the at least three antibodies or fragments thereof binds specifically to proteins AMCAR, CK 5/6, and HMWCK, for a sufficient time to form at least three different antigen-antibody complexes, b) detecting said at least three different antigen-antibody complexes, followed by, optionally, c) comparing the detected antigen-antibody complexes to a positive and/or negative control, and/or d) identifying the antigen-antibody complexes as proteins AMCAR, CK 5/6, and HMWCK.

A further aspect of the present invention provides a method for detection in vitro of prostate cancer, or prostatic intraepithelial neoplasia (PIN), or benign mimics of prostate cancer in a biological sample, the method comprising the steps of a) contacting said sample with a composition comprising at least three different primary antibodies or fragments thereof, wherein said antibodies or fragments thereof binds specifically to proteins AMCAR, CK 5/6, and HMWCK, for a sufficient time to form at least three different antigen-antibody complexes on the prostate cells, b) detecting said at least three antigen-antibody complexes, d) comparing the detected antigen-antibody complexes to a positive and/or negative control, thereby detecting the prostate cancer, or prostatic intraepithelial neoplasia (PIN), or benign mimics of prostate cancer.

A further aspect of the present invention provides a method for in vitro diagnosing and/or prognosing prostate cancer, or prostatic intraepithelial neoplasia (PIN), or benign mimics of prostate cancer in a biological sample, the method comprising the steps of a) contacting the sample with a composition comprising at least three different primary antibodies or fragments thereof, wherein said antibodies or fragments thereof binds specifically to proteins AMCAR, CK 5/6, and HMWCK, for a sufficient time to form at least three different antigen-antibody complexes, b) detecting said at least three antigen-antibody complexes, c) comparing the amount of antigen-antibody complexes detected to a positive and/or negative control, thereby diagnosing and/or prognosing the prostate cancer, or prostatic intraepithelial neoplasia (PIN), or benign mimics of prostate cancer.

A further aspect of the present invention provides an in vitro method for predicting outcome of treatment in a subject of prostatic cancer, or prostatic intraepithelial neoplasia (PIN), or benign mimics of prostate cancer patients, the method comprising the steps of a) detecting the expression of proteins AMCAR, CK 5/6, and HMWCK, b) comparing the expression of said proteins to a positive and/or negative control, thereby c) predicting the outcome of treatment of the prostate cancer, or prostatic intraepithelial neoplasia (PIN), or benign mimics of prostate cancer in said subject based on the detected expression of said three proteins.

A further aspect of the present invention provides an in vitro method of assessing efficacy of treatment of prostatic cancer, or prostatic intraepithelial neoplasia (PIN), or benign mimics of prostate cancer, the method comprising the steps of
- a) detecting proteins AMCAR, CK 5/6, and HMWCK,
- b) repeating step a) at one or more time points during treatment of said subject for prostatic cancer, or prostatic intraepithelial neoplasia (PIN), or benign mimics of prostate cancer, wherein a relative change in expression of proteins AMCAR, CK 5/6, and HMWCK over time indicates effective treatment.

A further aspect of the present invention provides an in vitro method for predicting outcome of treatment in a subject of prostatic cancer, or prostatic intraepithelial neoplasia (PIN), or benign mimics of prostate cancer patients, the method comprising the steps of
- a) providing a biological sample from a subject having prostatic cancer, or prostatic intraepithelial neoplasia (PIN), or benign mimics of prostate cancer,
- b) detecting the expression of proteins AMCAR, CK 5/6, and HMWCK,
- c) comparing the expression of said proteins to a positive and/or negative control, thereby
- d) predicting the outcome of treatment of the prostate cancer, or prostatic intraepithelial neoplasia (PIN), or benign mimics of prostate cancer in said subject based on the detected expression of said three proteins A further aspect of the present invention provides a an in vitro method of assessing efficacy of treatment of prostatic cancer, or prostatic intraepithelial neoplasia (PIN), or benign mimics of prostate cancer, the method comprising the steps of
- a) providing a biological sample from a subject having prostatic cancer, or prostatic intraepithelial neoplasia (PIN), or benign mimics of prostate cancer,
- b) detecting proteins AMCAR, CK 5/6, and HMWCK,
- c) repeating step a) at one or more time points during treatment of said subject for prostatic cancer, or prostatic intraepithelial neoplasia (PIN), or benign mimics of prostate cancer, wherein a relative change in expression of AMCAR, CK 5/6, and HMWCK over time indicates effective treatment.

A further aspect of the present invention provides a use of the composition according to the invention to detect proteins AMCAR, CK 5/6, and HMWCK.

A further aspect of the present invention provides a use of the composition according to the invention to detect prostate cancer or prostatic intraepithelial neoplasia (PIN), or benign mimics of prostate cancer.

A further aspect of the present invention provides a use of the composition to diagnose or prognose prostate cancer or prostatic intraepithelial neoplasia (PIN), or benign mimics of prostate cancer.

A further aspect of the present invention provides kits of the present invention.

FIGURES

Figure 3:
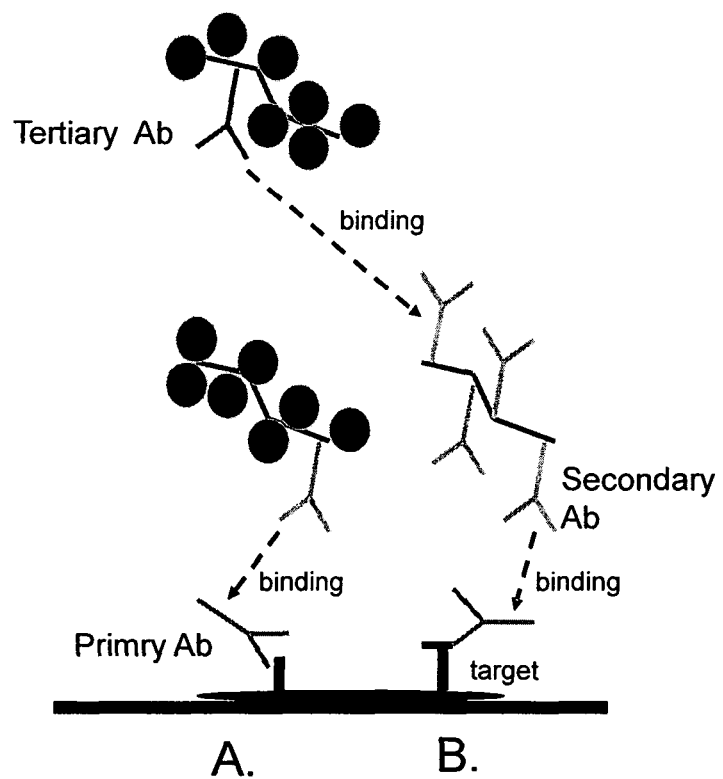

FIG. 3 shows two different examples of the composition according to the invention comprising primary antibodies binding to target i.e. binding respectively to AMCAR, HMWCK, and CK5/6. In one particular example the primary antibody is a mouse antibody or a rabbit antibody. Secondary antibodies may conjugated to linkers with a detection system optionally linked thereto or may be allowed to react with the tertiary antibody. In this picture, panel A shows a mouse anti-target antibody. The secondary step is a swine anti-mouse antibody conjugated with dextran and HPR (horse radish peroxidase). In panel B, the primary antibody binding the target is a rabbit antibody and the secondary antibody is a goat anti-rabbit antibody conjugated to dextran. In this panel, the third step, the tertiary antibody is a rabbit-anti goat antibody conjugated to dextran and alkaline phosphatase (AP). He two panels may, of course, co-exist in the composition according to the invention to allow both HRP and AP detection of two different targets in parallel. Further, the two panels are only exemplary and may be modified in different ways to allow parallel detection of the three different antigens of the composition according to the invention.

Figure 4:
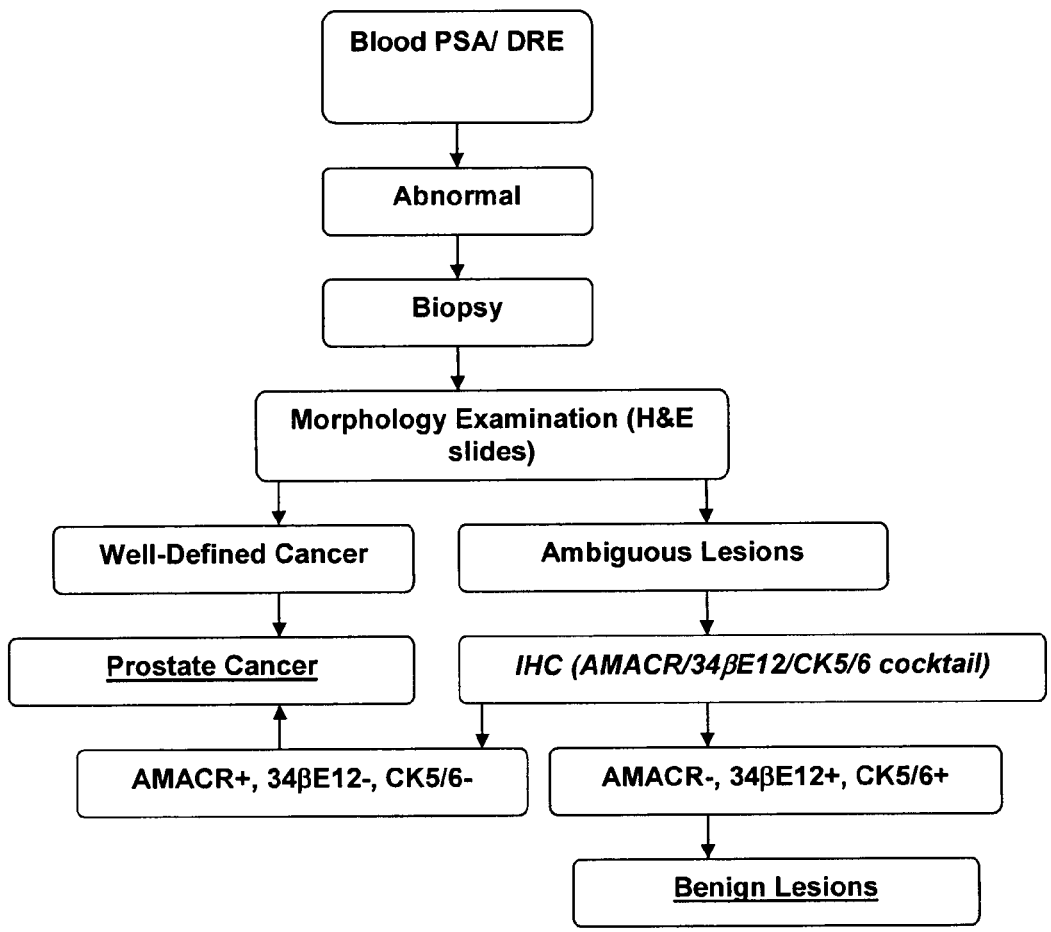

FIG. 4 shows a flow chart for diagnosis of prostate cancer using the composition according to the invention. After an initial blood analysis of PSA/DRE and the levels are found abnormal, a biopsy is taken. Morphological examinations using H&E (hematoxylin & eosin) staining identifies either well-defined cancer (Prostate cancer, underlined) or ambiguous lesions. The composition according to the invention may e.g. be used on the ambiguous lesions to identify prostate cancer being AMCAR+, HMWCK−, e.g. 34βE12−, and CK5/6− or benign lesions being AMCAR−, HMWCK+, e.g. 34βE12+, and CK5/6+.

Figure 5:
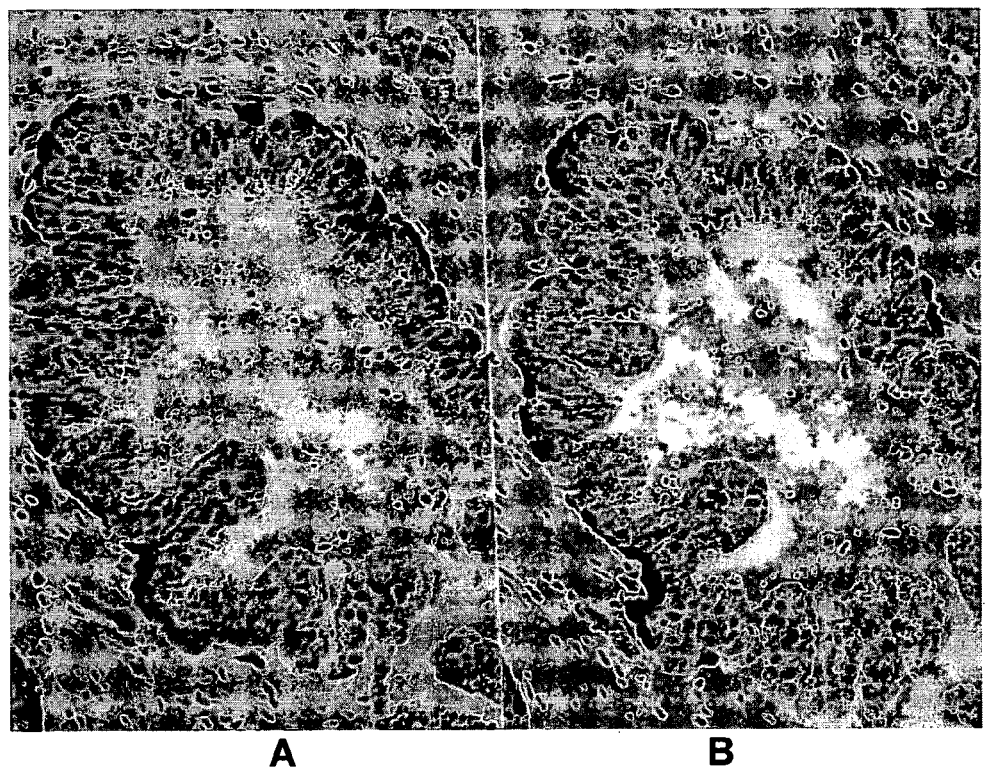

FIG. 5 shows the results of immunohistochemistry (IHC) stainings using an antibody cocktail of the invention comprising antibodies binding to AMCAR, HMWCK (clone 34βE12) and CK5/6 (A) compared to another antibody cocktail (PIN4, BioCare) comprising antibodies binding to AMCAR, CK5, CK14 and p63. More cells and stronger staining in the basal cell layer of the hyperplastic glands are seen in panel A compared to B. Arrows are pointing at the basal cell area showing fewer basal cells stained in panel B, compared to stained basal cells in panel A.

Figure 6:
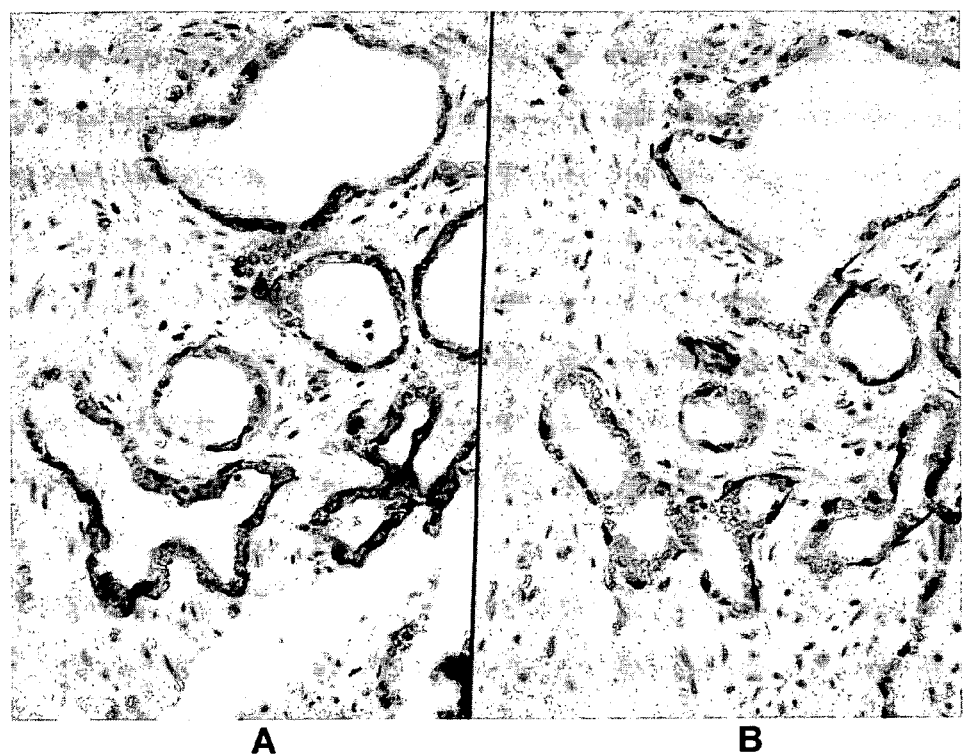

FIG. 6 shows the results of immunohistochemistry (IHC) stainings using an antibody cocktail of the invention comprising antibodies binding to AMCAR, HMWCK (clone 34βE12) and CK5/6 (A) compared to another antibody cocktail (PIN4, BioCare) comprising antibodies binding to AMCAR, CK5, CK14 and p63. More cells and stronger staining in the basal cell layer of the athrophy glands are seen in panel A compared to B.

Figure 7:
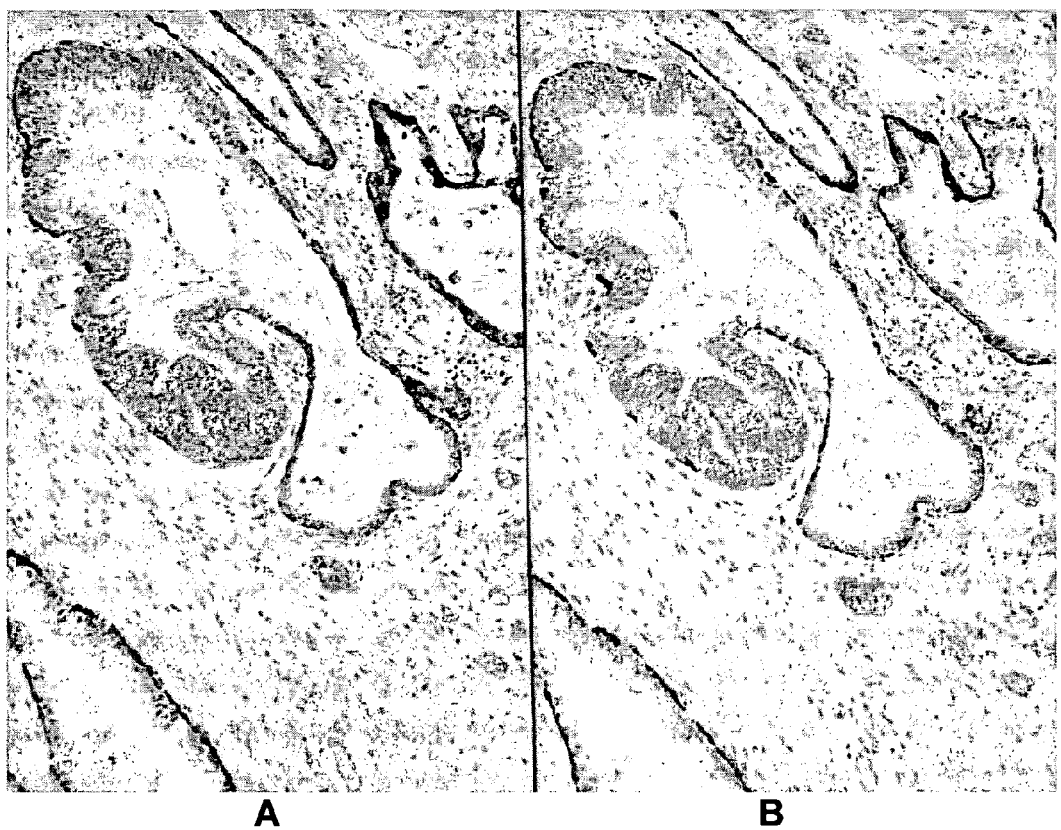

FIG. 7 shows the results of immunohistochemistry (IHC) stainings using an antibody cocktail of the invention comprising antibodies binding to AMCAR, HMWCK (clone 34βE12) and CK5/6 (A) compared to another antibody cocktail (PIN4, BioCare) comprising antibodies binding to AMCAR, CK5, CK14 and p63. More cells and stronger staining in the basal cell layer of the prostatic intraepithelial neoplasia (PIN) and athrophy gland are seen in panel A compared to B. Cancerous glands are lack of basal cells (arrow).

DETAILED DESCRIPTION OF THE INVENTION

Definitions

"Subject" as used herein, means any mammal including human having or suspected of having a disease.

"At least one" as used herein means one or more, i.e. 1, 2, 3, 4, 5, 6, 7, 8, 9, 10 etc.

"Detection", "detect", "detecting" as used herein includes qualitative and/or quantitative detection (measuring levels) with or without reference to a control, and further refers to the identification of the presence, absence, or quantity of a given protein, specifically the proteins AMCAR, CK 5/6, and HMWCK.

As used herein, the singular forms "a", "and", and "the" include plural referents unless the context clearly dictates otherwise. Thus, for example, reference to "an antibody" includes a plurality of such antibodies.

"Diagnosis" as used herein encompasses the identification of the nature of a disease.

"Prognosis" as used herein encompasses a forecast as to the probable outcome of a disease, the prospects as to recovery from a disease as indicated by the nature and symptoms of a disease.

"True positives" refers to those subjects having a localized or a metastasized prostate cancer.

"False negatives" refers to those subjects having either a localized or a metastasized prostate cancer and are not categorized as such by a diagnostic assay.

"True negatives" refers to those subjects who do not have a localized or a metastasized prostate cancer and who are categorized as such by a diagnostic assay.

"False positives" refers to those subjects who do not have a localized or a metastasized prostate cancer but are categorized by a conventional diagnostic assay as having a localized or metastasized prostate cancer.

Depending on context, the term "false positives" may also refer to those subjects who do not have prostate cancer but are categorized by a diagnostic assay as having prostate cancer or a non-malignant disease of the large intestine.

"Sensitivity", as used herein in the context of its application to diagnostic assays, refers to the proportion of all subjects with localized or metastasised prostate cancer that are correctly identified as such (that is, the number of true positives divided by the sum of the number of true positives and false negatives).

"Specificity" of a diagnostic assay, as used herein in the context of its application to diagnostic assays, refers to the proportion of all subjects with neither localized or metastasized prostate cancer that are correctly identified as such (that is, the number of true negatives divided by the sum of the number of true negatives and false positives).

The terms "neoplasm" or "tumor" may be used interchangeably and refer to an abnormal mass of tissue wherein the growth of the mass surpasses and is not coordinated with the growth of normal tissue. A neoplasm or tumor may be defined as "benign" or "malignant" depending on the following characteristics: degree of cellular differentiation including morphology and functionality, rate of growth, local invasion and metastasis. A "benign" neoplasm is generally well differentiated, has characteristically slower growth than a malignant neoplasm and remains localized to the site of origin. In addition a benign neoplasm does not have the capacity to infiltrate, invade or metastasize to distant sites. A "malignant" neoplasm is generally poorly differentiated (anaplasia), has characteristically rapid growth accompanied by progressive infiltration, invasion, and destruction of the surrounding tissue. Furthermore, a malignant neoplasm has the capacity to metastasize to distant sites.

The term "metastasis" refers to the spread or migration of cancerous cells from a primary (original) tumor to another organ or tissue, and is typically identifiable by the presence of a "secondary tumor" or "secondary cell mass" of the tissue type of the primary (original) tumour and not of that of the organ or tissue in which the secondary (metastatic) tumour is located. For example, a prostate cancer that has migrated to bone is said to be metastasized prostate cancer, and consists of cancerous prostate cancer cells in the large intestine as well as cancerous prostate cancer cells growing in bone tissue.

"Healthy" refers to a subject possessing good health. Such a subject demonstrates an absence of any malignant or non-malignant disease of the prostate. In the context of this application, a "healthy individual" is only healthy in that they have an absence of any malignant or non-malignant disease of the prostate; a "healthy individual" may have other diseases or conditions that would normally not be considered "healthy".

"Subject" as used herein denotes a mammal, such as a rodent, a feline, a canine, and a primate. Preferably a subject according to the invention is a human.

"Monoclonal antibody" or "mAb" as used herein refers to an antibody of a single amino acid composition, that is directed against a specific antigen and that is produced by a single clone of B cells or hybridoma.

"Polyclonal antibody" as used herein refers to an antibody that is directed against a specific antigen that is derived from different B-cell lines.

"Fab" as used herein refers to an antibody fragment having a molecular weight of about 50,000 Da and antigen binding activity, in which about a half of the N-terminal side of H chain and the entire L chain, among fragments obtained by treating IgG with a protease, papaine, are bound together through a disulfide bond.

"F(ab')$_2$" as used herein refers to an antibody fragment having a molecular weight of about 100,000 Da and antigen binding activity, which is slightly larger than the Fab bound via a disulfide bond of the hinge region, among fragments obtained by treating IgG with a protease, pepsin.

"Fab'" as used herein refers to an antibody fragment having a molecular weight of about 50,000 Da and antigen binding activity, which is obtained by cutting a disulfide bond of the hinge region of the F(ab')$_2$.

As used herein, a single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

"Hybridoma" as used herein denotes a cell, which is obtained by subjecting a B cell prepared by immunizing a non-human mammal with an antigen to cell fusion with a myeloma cell derived from a mouse or the like which produces a desired monoclonal antibody having an antigen specificity.

As used herein a "biological sample" encompasses a variety of sample types obtained from any subject having or not having prostate cancer. A typical subject is a human male; however, any mammal that has a prostate that may develop cancer can serve as a source of a biological sample useful in a disclosed method. Exemplary biological samples useful in the disclosed methods include but are not limited to biological samples disclosed herein such as e.g. solid tissue samples such as a biopsy specimen or tissue cultures or cells derived there from, and the progeny thereof. For example, biological samples include cells obtained from a tissue sample collected from an individual suspected of having a prostate cancer. Therefore, biological samples encompass clinical samples, cells in culture, cell supernatants, cell lysates, and tissue samples, e.g. a transrectal prostate biopsy.

Further examples are prostate biopsies and/or prostatectomy tissues, or prostate cell samples (such as can be collected by prostate massage, in the urine, or in fine needle aspirates). Samples may be fresh or processed post-collection (e.g., for archiving purposes). In some examples, processed samples may be fixed (e.g., formalin-fixed) and/or wax- (e.g., paraffin-) embedded. Fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, Histotechnology: A Self-Instructional Text, Chicago: ASCP Press, 1997). In some examples, the sample (or a fraction thereof) is present on a solid support.

Solid supports useful in a disclosed method need only bear the biological sample and, optionally, but advantageously, permit convenient detection of the proteins of interest in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE® chips.

"Treatment" as used herein is defined as the management of a patient through medical or surgical means. The treatment improves or alleviates at least one symptom of a medical condition or disease and is required to provide a cure. The term "treatment outcome" or "outcome of treatment" as used herein is the physical effect upon the patient of the treatment.

The term "algorithm" as used herein refers to a mathematical formula that provides a relationship between two or more quantities. Such a formula may be linear, or non-linear, and may exist as various numerical weighting factors in computer memory.

"Prostate cancer" refers to a neoplasm, e.g., malignant neoplasm, of the prostate within a given subject, wherein the neoplasm is of epithelial origin. The term "prostate cancer", when used without qualification, includes both localized and metastasized prostate cancer. The term "prostate cancer" can be qualified by the terms "localized" or "metastasized" to differentiate between different types of tumor, where a "localized" refers to the original mother tumour, and the metastasized to the tumours that has spread from the original mother tumour.

The term "stage of prostate cancer" as used herein can be defined by one of a number of accepted systems for classifying the progression of prostate cancer. For example, the Jewett-Whitmore system classifies prostate cancer first as stage A, B, C, or D. Stages A and B cancers are considered curable. Stages C and D are treatable, but their prognoses are discouraging. A number is then assigned to describe specific conditions within each stage. For example, a tumor classified as stage BI is a single cancerous nodule confined to one lobe of the prostate. More specifically, the stages are defines as follows: Stage A is very early and without symptoms; cancer cells confined to the prostate; Stage AI is well differentiated and slightly abnormal cancer cells; stage A2 is moderately or poorly differentiated and abnormal cancer cells in several locations within the prostate; stage B is confined to the prostate, but palpable (detectable by digital rectal exam) and/or detectable by elevated PSA; stage BO is confined to the prostate, non-palpable; PSA elevated; stage BI is a single cancerous nodule in one lobe of the prostate; stage B2 is extensive, involvement in one or both prostate lobes. Stage C is cancer cells found outside the prostate capsule (membrane covering the prostate); spread confined to surrounding tissues and/or seminal vesicles; stage CI extends outside the prostate capsule; and stage C2 has bladder or urethral obstruction. Stage D has metastasis (spread) to regional lymph nodes, or to distant bones, organs (e.g., liver, lungs), and/or other tissues; stage DO is metastatic, clinically localized, and showing elevated blood PAP levels; stage DI has regional lymph nodes involved; stage D2 has distant lymph nodes, bones, or organs involve; and stage D3 has metastatic disease after treatment.

Alternatively, the TNM System may be used to stage prostate cancer. The TNM (tumor, node, metastases) system stages are similar to those of the Jewett-Whitmore system, but with more specific alphanumeric subcategories. Stages of prostate cancer according to the TNM system are Primary tumor (T), TX: tumor cannot be assessed; TO: no evidence of primary tumor; TI: clinically not palpable or visible by imaging; TIa: found incidental to other surgery; present in 5% or less of tissue; TIb: found incidental to other surgery; present in 5% or more of tissue; Tie: identified by needle biopsy; T2: tumor confined within prostate; T2a: involving half a lobe or less of prostate; T2b: involving half a lobe; T2c: involving both lobes; T3: tumor extends through prostate capsule; T3a: extends through one lobe; T3b: extends through both lobes; T3c extends into seminal vesicles; T4: involves structures other than seminal vesicles; T4a: invades bladder neck, external sphincter, or rectum; and T4b: invades muscles and/or pelvic wall.

In the methods and uses disclosed where protein expression of AMCAR, CK 5/6 and HMWCK is determined by immunohistochemistry a scoring of protein expression may optionally be used. The scoring may be semi-quantitative; for example, with protein expression levels recorded as 0, 1, 2, or 3 (including, in some instances plus (or minus) values at each level, e.g., 1+, 2+, 3+) with 0 being substantially no detectable protein expression and 3 (or 3+) being the highest detected protein expression. In such methods, an increase or decrease in the corresponding protein expression is measured as a difference in the score as compared the applicable control (e.g. a standard value or a control sample); that is, a score of 3+ in a test sample as compared to a score of 0 for the control represents increased protein expression in the test sample, and a score of 0 in a test sample as compared to a score of 3+ for the control represents decreased protein expression in the test sample.

Immunohistochemistry (IHC) is one exemplary technique useful for detecting protein expression of AMCAR, CK 5/6, and HMWCK in the disclosed methods and uses. Antibodies (e.g., monoclonal and/or polyclonal antibodies) specific for each protein expression marker are used to detect the expression. The composition of the invention thus provides antibodies binding to of AMCAR, CK 5/6, and HMWCK. The antibodies can be detected, as further described herein, by direct labelling of the antibodies themselves, for example, with radioactive labels, fluorescent labels, hapten labels such as, biotin, or an enzyme such as horseradish peroxidase or alkaline phosphatase. Alternatively, an indirect labelling is used where unlabeled primary antibody is used in conjunction with a labelled secondary antibody, comprising e.g. antiserum, polyclonal antiserum or a monoclonal antibody specific for the primary antibody. IHC protocols are well known in the art and are commercially available, see e.g. Antibodies: A Laboratory Manual, Harlow and Lane (Cold Spring Harbor Laboratory press, Cold Spring Harbor, N.Y. 1988) and Current Protocols in Immunology, and Current Protocols in Molecular Biology, both John Wiley and Sons, Inc., N.Y.) incorporated herein by reference.

FIG. 4 shows in a flow chart an outline of a possible route for diagnosis of prostate cancer using the composition of the invention.

As revealed above, the present invention provides a means and methods to improve sensitivity and specificity of prostate cancer cell diagnosis and/or prognosis. More specifically, the present invention provides a composition that better sensitivity for detection of basal prostate cells so as to improve the detection of prostate cells in IHC, thereby giving a more consistent and reliable result when performing diagnosis and/or prognosis of prostate cancer or prostatic intraepithelial neoplasia (PIN), or benign mimics of prostate cancer patients.

Further, the composition according to the invention will improve the identification of prostate cancer, prostatic intraepithelial neoplasia (PIN), and benign mimics of prostate cancer compared to available methods.

The composition disclosed herein thus shows an improved staining for the detection of various prostate lesions when compared to other known antibody cocktails such as e.g. AMCAR+CK5+CK14+p63 or AMCAR+34βE12+p63 (Bio-Care PIN 4-cocktail), AMCAR+34βE12, and AMCAR+34βE12+p63 (see e.g. FIGS. 1-2, and 5-7 and Examples given herein).

The composition will stain and detect normal components of the prostate. Basal cells with antibody binding specifically to CK 5/6 and HMWCK. The combination of antibodies binding specifically to the two proteins will identify basal cells expressing cytokeratins 1, 5, 10, 6, and 14.

FIG. 4 shows that prostate cancer is identified as AMCAR+, 34βE12−, CK5/6− and that benign lesions are identified as AMCAR−, 34βE12+, and CK5/6+.

The composition further stains and detects prostatic intraepithelial neoplasia (PIN) and prostate cancer with antibodies binding specifically to the protein AMCAR.

Particularly, the composition according to the invention may enable accurate and less biased measurements of the basal cell compartment of the biological sample (see e.g. examples herein). Particularly, the composition enables more than 1, 1.3, 1.5, 2% or more, for example 5, 10, 15, 20, 25, 30, 35, 40, 45, or even 50% more positive basal cell areas of the biological sample compared to the individual antibodies or excising antibody cocktails such as a cocktail of HMWCK & anti-p63.

Further, the basal cell area detected with the composition of the present invention will provide staining of more basal cells, than a p63 cocktail in the art. Thus, the composition allows an improved detection of basal cells in prostate tissue which aids in the identification of prostate cancer, prostatic intraepithelial neoplasia (PIN) and benign mimics of prostate cancer. Particularly, improving the detection of basal cells in prostate tissue will improve identification of the glands in the prostate tissue, thereby identifying in a reliable and accurate way prostate cancer, prostatic intraepithelial neoplasia (PIN) and benign mimics of prostate cancer. Particularly, detection of both AMCAR and CK 5/6 in a biological sample detects more basal cells, such as 5, 10, 20, 30, 40, and even 50%, more basal cells than the in the art excising antibody cocktails comprising p63 instead of CK 5/6.

The composition of the invention further improves the sensitivity and specificity of detecting prostate cancer.

According to the invention, in some embodiments the sensitivity is improved to about 95, 96, 97, 98, 99, 99.5, 99.9 or even about 100% compared to antibody cocktails used in the art to detect prostate cancer, prostatic intraepithelial neoplasia (PIN) and benign mimics of prostate cancer, or compared to H&E (haematoxylin & eosin) staining.

Similarly, further embodiments improve the specificity is improved to about 80, 85, 89, 90, 95, 96, 97, 98, 99, 99.5, 99.9 or even about 100% compared to antibody cocktails used in the art to detect prostate cancer, prostatic intraepithelial neoplasia (PIN) and benign mimics of prostate cancer, or compared to H&E staining.

The Proteins

The present invention encompass a composition comprising at least three different primary antibodies or fragments thereof, wherein the at least three different antibodies binds or fragments thereof binds specifically to HMWCK, AMCAR and CK 5/6. As an example, at least one first primary antibody binds specifically to HMWCK, at least one second primary antibody binds specifically to AMCAR, and at least one third primary antibody binds CK 5/6. Thus, the at least three antibodies are in an antibody cocktail either in a format ready-to-use by the user or in a concentrated solution and required a dilution before its use, some times referred to as a stock solution.

HMWCK is High Molecular Weight Cytokeratin are intermediate filament cytoskeletal proteins essential to development and differentiation of epithelial cells. Approximately twenty different cytokeratins have been identified and are classified and numbered according to molecular weight and isoelectric points. In general, most low molecular weight cytokeratins (40-54 kD) are distributed in nonsquamous epithelium, Moll's catalog numbers 7-8 and/or 17-20 (see Moll R, Franke W W, Schiller D L, Geiger B, Krepler R., Cell, 1982 November; 31(1):11-24). High molecular weight cytokeratins (48-67 kD) are found in the squamous epithelium, Moll's catalog numbers 1-6 and/or 9-16 (15). A preferred antibody is mouse monoclonal antibody 34βE12 produced by clone 34βE12 available from DAKO.

Cytokeratin 5/6 is a high molecular weight, basic type of cytokeratin, with a molecular mass of 58 kDa, expressed in the basal, the intermediate and the superficial cell layers of stratified epithelia as well as in transitional epithelia, complex epithelia, and in mesothelial cells and mesothelioma. CK 5 has not, with few exceptions, been found in simple epithelia and in non-epithelial cells. CK 6 is also a high molecular weight, basic type of cytokeratin, with a molecular mass of 56 kDa, expressed by proliferating squamous epithelium often paired with CK 16 (48 kDa). An example of suitable antibody is the mouse Anti-Human Cytokeratin 5/6, produced by clone D5/16 B4, available from DAKO.

AMCAR is a prostate cancer-specific protein expressed by the P504s gene. The gene encodes a protein involved in the beta-oxidation of branched chain fatty acids, namely Alpha-methylacyl Co-enzyme A racemase, AMCAR (synonyms p504S, a-methylacyl-CoA). An example of suitable antibody is the rabbit anti-AMACR, produced by clone 13H4, available from DAKO. This particular antibody recognizes a 382 amino acid protein that was identified by cDNA library subtraction in conjunction with high throughput microarray screening of prostate adenocarcinoma (6). Alpha-methylacyl-CoA racemase (AMACR) is an enzyme that is involved in bile acid biosynthesis and β-oxidation of branched-chain fatty acids. AMACR is expressed in cells of premalignant high grade prostatic intraepithelial neoplasia (HGPIN) and prostate adenocarcinoma, but is present at low or undetectable levels in glandular epithelial cells of normal prostate and benign prostatic hyperplasia.

An Antibody Cocktail

In one aspect the present invention provides a composition comprising at least three primary antibodies or fragments thereof, wherein the at least three antibodies or fragments thereof binds specifically to at least three different proteins, and wherein the at least three different proteins are AMCAR, CK 5/6, and HMWCK. Thus, the composition comprises one first primary antibody reacting specifically with, i.e. binding specifically to, a first protein, a second primary antibody reacting specifically with a second protein and a third primary antibody reacting specifically with a third protein.

In one embodiment, the first protein is AMCAR, the second protein is CK5/6, and the third protein is HMWCK. It should be noted that both CK5/6 and HMWCK both represent groups of proteins to which an antibody reacts due to similar antigenic structure, i.e. the part that an antibody recognises sterically. However, due to similar spatial form of the antigen determinant, i.e. the antibody-binding domain of the antigen, an antibody binding to CK 5 also binds CK 6, thus grouped into CK5/6. Similarly, HMWCK refers to high molecular weight cytokeratins (48-67 kD) found in the squamous epithelium, Moll's catalogue numbers 1-6 and/or 9-16.

By "reacting specifically with" as used herein it is intended to equal "capable of binding selectively" or "binding specifically to". As used herein the expressions are intended to mean that the antibody or antigen-binding fragment, or variant, fusion or derivative thereof, including any anti-body derived binding moiety, which is capable of binding to an antigen of a molecule and further which binds at least 10-fold more strongly the proteins AMCAR, CK 5/6, and HMWCK than to another proteins for example at least 50-fold more strongly or at least 100-fold more strongly. The binding moiety may be capable of binding selectively to the protein under physiological conditions, e.g. in vivo. Suitable methods for measuring relative binding strengths include, immunoassays, for example where the binding moiety is an antibody (see Harlow & Lamp; Lane, "Antibodies: A Laboratory", Cold Spring Harbor Laboratory Press, New York, which is incorporated herein by reference). Alternatively, binding may be assessed using competitive assays or using Biacore® analysis (Biacore International AB, Sweden).

In one aspect embodiment, the antibody or antigen-binding fragment, or variant, fusion or derivative thereof, binds exclusively to a protein of the present invention.

One embodiment is wherein the composition comprises a first primary antibody reacting specifically with AMCAR, a second primary antibody reacting specifically with CK 5/6, and a third primary antibody reacting specifically with HMWCK.

In one embodiment, the first antibody is monoclonal antibody rabbit anti-AMCAR produced by clone 13H4 reacting specifically with AMCAR.

In still a further embodiment, the second antibody is a monoclonal mouse-anti-human cytokeratin 5/6 produced by clone D5/16 B4 reacting specifically with CK 5/6.

In still a further embodiment, the third antibody is a monoclonal antibody produced by clone HMWCK reacting specifically with HMWCK.

One further embodiment is wherein the first primary antibody is monoclonal antibody rabbit anti-AMCAR produced by clone 13H4 reacting specifically with AMCAR, a second primary antibody is a monoclonal mouse-anti-human cytokeratin 5/6 produced by clone D5/16 B4 reacting specifically with CK 5/6, and a third primary antibody is a monoclonal antibody produced by clone HMWCK reacting specifically with HMWCK. The antibodies are present in a composition according to the invention. The composition may in further aspects of the present invention be an antibody cocktail, in aqueous form or in a freeze dried powder form. For the latter, a re-hydration step is required to put the antibodies in a usable liquid form before The antibodies may be whole antibodies or fragments thereof, e.g. antigen-binding fragment, or variant, fusion or derivative thereof as long as they are capable of binding to the desired protein in vitro. Such binding specificity may be determined by methods well known in the art, such as e.g. ELISA, immunohistochemistry, immunoprecipitation, Western blots, chromatography and flow cytometry using transfected cells expressing the all subunit or a heterodimer thereof (see Examples). Examples of how to measure specificity of an antibody is given in e.g. Harlow & Lane, "Antibodies: A Laboratory", Cold Spring Harbor Laboratory Press, New York, which is incorporated herein by reference.

By "antibody" we include substantially intact antibody molecules of any species such as rodents, e.g. murine, rat, guneapig, or non-rodents such as rabbit, goat, sheep, dog, pig, camel, dromedary, donkey, horse or chicken, as well as chimaeric antibodies, humanized antibodies, human antibodies (wherein at least one amino acid is mutated relative to the naturally occurring human antibodies), single chain antibodies, bispecific antibodies, antibody heavy chains, antibody light chains, homo-dimers and hetero-dimers of antibody heavy and/or light chains, and antigen binding fragments and derivatives of the same. For example, the antibody may be a monoclonal antibody.

Antigenic specificity is conferred by variable domains and is independent of the constant domains, as known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the V H and V L partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

Thus, by "antigen-binding fragment" we mean a functional fragment of an antibody that is capable of binding to any of the proteins AMCAR, CK 5/6, and HMWCK.

Exemplary antigen-binding fragments may be selected from the group consisting of Fv fragments (e.g. single chain Fv and disulphide-bonded Fv), Fab-like fragments (e.g. Fab fragments, Fab' fragments and F(ab) 2 fragments), single antibody chains (e.g. heavy or light chains), single variable domains (e.g. VH and VL domains) and domain antibodies (dAbs, including single and dual formats; i.e. dAb-linker-dAb).

Thus, in one embodiment the antibody or antigen-binding fragment, or variant, fusion or derivative thereof, comprises or consists of an intact antibody. In one embodiment, the antibody is a monoclonal antibody.

For example, the antibody or antigen-binding fragment, or a variant, fusion or derivative thereof, may consist essentially of an intact antibody. By "consist essentially of" we mean that the antibody or antigen-binding fragment, variant, fusion or derivative thereof consists of a portion of an intact antibody sufficient to retain binding specificity for any of the three different proteins AMCAR, CK 5/6, and HMWC. In further embodiments, the three different proteins AMCAR, CK 5/6, and HMWC are of human origin.

The term 'antibody' also includes all classes of antibodies, including IgG, IgA, IgM, IgD and IgE. In one embodiment, however, the antibody is an IgG molecule, such as an IgGl, IgGl, IgG3, or IgG4 molecule.

In one embodiment, the antibody is an IgG1 molecule. In a further embodiment, the antibody is a IgG1 molecule with a kappa light chain.

In a further embodiment, the antibody is a non-naturally occurring antibody. Of course, where the antibody is a naturally occurring antibody, it is provided in an isolated form (i.e. distinct from that in which it is found in nature).

Also included within the scope of the invention are modified versions of antibodies and antigen-binding fragments thereof, e.g. modified by the covalent attachment of polyethylene glycol or other suitable polymer, and uses of the same.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. Proc. Natl. Acad. Sci. U.S.A., vol 86, pages 3833-3837; Winter et al, 1991, Nature 349:293-299, which are incorporated herein by reference) or generation of monoclonal antibody molecules by cell lines in culture. These include, but are not limited to, the hybridoma technology, the human B-cell hybridoma technology, and the Epstein-Barr virus (EBV)-hybridoma technology (see Kohler et al, 1975. Nature 256: 4950497; Kozbor et al, 1985. J Immunol. Methods 81:31-42; Cote et al, 1983. Proc. Natl. Acad. Sci., USA 80:2026-2030; Cole et al, 1984. Mol Cell. Biol. 62:109-120, which are incorporated herein by reference).

For example, generating monoclonal or poloclonal antibodies to AMCAR, C/K 5/6 or HMWCK may be done by immunization where the whole protein or a suitable fragment thereof can be injected into non-human mammals (such as mice or rabbits), followed by boost injections, to produce an antibody response. Serum isolated from immunized animals may be isolated for the polyclonal antibodies contained therein, or spleens from immunized animals may be used for the production of hybridomas and monoclonal antibodies.

In one example, a monoclonal antibody to one of the proteins can be prepared from murine hybridomas according to the classical method of Kohler and Milstein {Nature, 256: 495, 1975) or derivative methods thereof. Briefly, a mouse (such as Balb/c) is repetitively inoculated with a few micrograms of the selected protein or peptide fragment thereof or a suitable carrier conjugate thereof over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued.

Antibody-producing clones are identified by detection of antibody in the supernatant fluid of the wells by immunoassay procedures, such as ELISA, as originally described by Engvall (Enzymol., 70:419, 1980), and derivative methods thereof.

Selected positive clones can be expanded and their monoclonal antibody product harvested for use.

Commercial sources of antibodies include DAKO A/S, Abcam, Lab Vision, BioCare Medical, Cell Marque Corp., etc.

Polyclonal antibody-producing animals are identified by bleeding immunised animals and selection of appropriate animal with ha suitable polyclonal antibody-titer thereof.

In some embodiments, antibodies are purified before use. Purification of antibodies are done using techniques available in the art and described in e.g. "Monoclonal Antibodies: A manual of techniques", H Zola (CRC Press, 1988) and in "Monoclonal Hybridoma Antibodies: Techniques and Applications", J G R Hurrell (CRC Press, 1982), which are incorporated herein by reference.

Generation of antibodies to AMCAR, C/K 5/6 and HMWCK are described in the art and available from commercial sources as described herein, or being available using techniques known to a skilled artisan using references enclosed herein and accordingly incorporated herein by reference.

The antibody or antigen-binding fragment or derivative thereof may also be produced by recombinant means. Suitable monoclonal antibodies to selected antigens and proteins may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982), and "Antibodies: A Laboratory Manual", Cold Spring Harbor Laboratory, New York, which are incorporated herein by reference.

Antibody fragments can also be obtained using methods well known in the art (see, for example, Harlow & Lane, 1988, "Antibodies: A Laboratory Manual", Cold Spring Harbor Laboratory, New York, which is incorporated herein by reference). For example, antibody fragments may be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

Thus, in one embodiment the composition provided herein is a composition wherein at least one of the primary antibodies is a monoclonal antibody.

In a further embodiment the composition provided herein is a composition wherein at least one of the primary antibodies is a recombinant antibody.

The composition described herein may be lyophilized for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilized (freeze dried) composition loses no more than about 20%, or no more than about 25%, or no more than about 30%, or no more than about 35%, or no more than about 40%, or no more than about 45%, or no more than about 50% of its activity (prior to lyophilisation) when re-hydrated. It will be further appreciated by persons skilled in the art that the antibodies and antigen-binding fragments, variants, fusions and derivatives thereof, described herein may exist in monomeric form or in the form of a homo- or hetero-multimer thereof (e.g. dimer, trimer, tetramer, pentamer, etc.).

Further provided herein is that the primary antibodies or fragments thereof may be labelled directly or indirectly, with a detectable moiety. By directly labeled is meant that the detectable moiety is attached to the antibody. By indirect labeled it is meant that the detectable moiety is attached to a linker, such as, for example, a secondary or tertiary antibody. The detectable moiety may be any moiety or marker known to those skilled in the art, or as described herein, and as being such a moiety being capable of generating a signal that allows the direct or indirect quantitative or relative measurement of a molecule to which it is attached.

A wide variety of detectable moieties, or labels, and conjugation techniques are known and reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; 4,366,149 and 4,366,241 (all incorporated herein by reference). Also, recombinant immunoglobulins may be used and labelled (see U.S. Pat. No. 4,816,576, incorporated herein by reference).

The detectable moiety may be a single atom or molecule which is either directly or indirectly involved in the production of a detectable species. Optionally, the detectable moiety is selected from the group consisting of a fluorescent moiety, an enzyme linked moiety, a biotinylated moiety and a radiolabeled moiety, as described further herein, e.g. below. By "label", "detectable moiety" is meant any detectable tag that can be attached directly (e.g., a fluorescent molecule integrated into a polypeptide) or indirectly (e.g., by way of binding to a primary antibody with a secondary, tertiary or further antibody with an integrated fluorescent molecule) to the molecule of interest. Thus, a label, marker or detectable moiety is any tag that can be visualized, for example, with imaging methods.

By a "detectable moiety" we further include the meaning that the moiety is one which, when located at the target site following providing the composition of the invention to a biological sample, such as a tissue sample, e.g. a human prostate tissue sample, may be detected in vitro. That includes that the detectable moiety is signal generating and it is further convenient and thus included in further embodiments if the detectable moiety may be detected and the relative amount and/or location of the moiety (for example, the location on an tissue sample) may be determined. Detectable moieties are well known in the art.

Thus, the composition of the invention is useful in methods further exemplified herein by methods and uses for detection of AMCAR, CK 5/6, HMWCK, diagnosis or prognosis prostatic cancer in vitro of biological samples. In further embodiments, image systems are used exemplified further herein.

Suitable detectable moieties are well known in the art and the attachment or linking of these moieties to polypeptides and proteins is further well known in the art. Further examples of detectable moieties are an enzyme; an enzyme substrate; an enzyme inhibitor; coenzyme; enzyme precursor; apoenzyme; fluorescent substance; pigment; chemiluminescent compound; luminescent substance; coloring substance; magnetic substance; or a metal particle such as gold colloid; a radioactive substance such as 125I, 131I, 32P, 3H, 35S, or 14C; a phosphorylated phenol derivative such as a nitrophenyl phosphate, luciferin derivative, or dioxetane derivative; or the like. The enzyme may be a dehydrogenase; an oxidoreductase such as a reductase or oxidase; a transferase that catalyzes the transfer of functional groups, such as an amino; carboxyl, methyl, acyl, or phosphate group; a hydrolase that may hydrolyzes a bond such as ester, glycoside, ether, or peptide bond; a lyases; an isomerase; or a ligase. The enzyme may also be conjugated to another enzyme. The enzyme may be detected by enzymatic cycling. For example, when the detectable label is an alkaline phosphatase, a measurements may be made by observing the fluorescence or luminescence generated from a suitable substrate, such as an umbelliferone derivative. The umbelliferone derivative may comprise 4-methyl-umbellipheryl phosphate. The fluorescent or chemiluminescent label may be a fluorescein isothiocyanate; a rhodamine derivative such as rhodamine B isothiocyanate or tetramethyl rhodamine isothiocyanate; a dancyl chloride (5-(dimethylamino)-I-naphtalenesulfonyl chloride); a dancyl fluoride; a fluorescamine (4-phenylspiro&Isqb;furan-2(3H); Iy-(3yH)-isobenzofuran]-3;3y-dione); a phycobiliprotein such as a phycocyanine or physoerythrin; an acridinium salt; a luminol compound such as lumiferin, luciferase, or aequorin; imidazoles; an oxalic acid ester; a chelate compound of rare earth elements such as europium (Eu), terbium (Tb) or samarium (Sm); or a coumarin derivative such as 7-amino-4-methylcoumarin. The label may also be a hapten, such as adamantine, fluoroscein isothiocyanate, or carbazole. The hapten may allow the formation of an aggregate when contacted with a multi-valent antibody or (strep)avidin containing moiety. Further examples of detectable moieties include, but are not limited to, the following: radioisotopes (e.g. 3H, 14C3 35S, 123I, 125I, 131I 99Tc, 111In, 90Y, 188Re), radionuclides (e.g. 11C, 18F, 64Cu), fluorescent labels (e.g. FITC, rhodamine, lanthanide phosphors, carbocyanine), enzymatic labels (e.g. horseradish peroxidase, β-galactosidase, luciferase, alkaline phosphatase), chemiluminescent, biotinyl groups and predetermined polypeptide epitopes recognised by a secondary binding entity (e.g. leucine zipper pair sequences, binding sites for secondary antibodies, metal binding domains, epitope or protein tags, carbohydrates). In some embodiments, labels are attached by spacer arms of various lengths to reduce potential steric hindrance.

In indirect labelling, an additional molecule or moiety is brought into contact with, or generated at the site of, the antibody-antigen complexes, i.e. immune-complexes, between the primary antibody and the protein it binds to. For example, a detectable moiety such as an enzyme can be attached to or associated with the detecting antibody or detecting molecule as exemplified herein. The signal-generating molecule can then generate a detectable signal at the site of the immune-complex. For example, an enzyme, when supplied with suitable substrate, can produce a visible or detectable product at the site of the immune-complex.

As another example of indirect labelling, an additional molecule (which can be referred to as a binding agent) that can bind to either the molecule of interest or to the antibody (primary antibody) of interest, such as a second antibody to the primary antibody, can be contacted with the immunocomplex. The additional molecule can have signal-generating molecule or detectable moiety.

The additional molecule may be an antibody, which can thus be termed a secondary, tertiary or further antibody. Binding of a secondary antibody to the primary antibody can form a so-called sandwich with the first (or primary) antibody and the molecule of interest. The immune-complexes can be contacted with the labelled, secondary antibody under conditions effective and for a period of time sufficient to allow the formation of secondary immune complexes. The secondary immune complexes can then be generally washed to remove any non-specifically bound labelled secondary antibodies, and the remaining label in the secondary immune complexes can then be detected. The additional molecule can also be or include one of a pair of molecules or moieties that can bind to each other, such as the biotin/avadin molecules, and the detecting antibody or detecting molecule should then include the other member of the pair.

Further examples of indirect labelling include the detection of primary antibody-antigen (immune-complexes) by a two step approach. For example, a molecule (which can be referred to as a first binding agent), such as an antibody, that has binding affinity for the primary immune complex between the primary antibody-antigen complex can be used to form secondary complexes, e.g. if a secondary antibody, secondary immune-complexes, as described above. After washing, the secondary complex can be contacted with another further molecule (which can be referred to as a second binding agent) that has binding affinity for the first binding agent, again under conditions effective and for a period of time sufficient to allow the formation of tertiary complexes, e.g. if antibody a tertiary immune-complex. In this example the second binding agent may be linked to a detectable moiety, allowing detection of the tertiary complexes thus formed. This system may further comprise means to provide for signal amplification.

Other examples of primary, secondary or further binding agents with means for signal amplification are conjugated anti-immunoglobulins such as biotinylated antibodies (e.g., conjugated with avidin/streptavidin) or staphylococcal Protein A (binds IgG), Protein G, dextran, aptamers, proteins, peptides, small organic molecules, natural compounds (e.g. steroids), non-peptide polymers, or any other molecules that specifically and efficiently bind to other molecules conjugated with a detectable moiety of not.

In one further embodiment, a secondary, tertiary or further binding agent is an antibody such as an anti-mouse conjugate, e.g. a swine anti-mouse antibody. The conjugate may be a conjugate to dextrane, HRP, biotin, alkali phosphatase, etc. as described supra.

In one embodiment the detectable moiety is a swine anti-mouse antibody conjugated with dextran and HRP.

In a further embodiment a secondary, tertiary or further binding agent is an antibody such as an anti-rabbit conjugate, e.g. a goat anti-rabbit conjugate. The conjugate may be a conjugate to dextrane, HRP, biotin, etc. described supra.

In one embodiment, the detectable moiety is a goat anti-rabbit conjugated with dextran.

In a further embodiment a secondary, tertiary or further binding agent is an antibody such as an anti-goat conjugate, such as e.g. a rabbit anti-goat conjugate. The conjugate may be a conjugate to dextrane, HRP, biotin, etc. described supra.

In one embodiment the detectable moiety is rabbit anti-goat conjugated with dextran and Alkaline phosphatase, AP.

In still a further embodiment, the composition provided herein further comprises a buffer. Examples of buffers are Tris-buffers such as Tris-HCl, and PBS-buffers. Suitable buffers are available and known in the art and examples are given in e.g. Antibodies: A Laboratory Manual, Harlow and Lane (Cold Spring Harbor Laboratory press, Cold Spring Harbor, N.Y. 1988) and Current Protocols in Immunology, and Current Protocols in Molecular Biology, both John Wiley and Sons, Inc., N.Y.) incorporated herein by reference. Further examples of buffers are given in e.g. U.S. Ser. No. 10/784,163 incorporated herein by reference.

Further additives to the buffers may be e.g. Tween® 20, BSA, sodium azide, glycerol, and water, and a pH from about 5.5 to about 7.5, such as about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5.

The antibody composition may when in a liquid form be provided in a "ready-to-use" form or in a concentrated form which may be diluted before use in any appropriate buffer system upon use, for example at least 1×10, 1×20, 1×30, 1×40, 1×50, 1×60, 1×70, 1×80, 1×90, 1×100, 1×150, 1×200, 1×250, 1×300, 1×350, 1×400, 1×450, 1×500, 1×550, 1×600, 1×650, 1×700, 1×750, 1×800, 1×900, 1×1000, 1×1200, 1×1500, 1×2000, 1×3000, 1×4000, 1×5000, 1×6000, 1×7000, 1×8000, 1×9000, 1×10000 and all ranges and values there between such as in e.g. the buffer systems provided here in or ant that may be apparent to a person skilled in the art.

The composition according to the invention may also be used alone or in combination with other means for detecting prostate cancer, including, but not limited to means for detecting and measuring Prostate Specific Antigen (PSA).

Methods and Uses of the Composition

The herein described composition may be used in various immuno-methods, such as immunohistochemical methods. General protocols for such immuno-methods, particularly immunohistochemistry methods, are known in the art (Antibodies: A Laboratory Manual, Harlow and Lane, Cold Spring Harbor Laboratory press, Cold Spring Harbor, N.Y. 1988, Current Protocols in Immunology, Unit 21.4, 2003, and Current Protocols in Molecular Biology, Unit 14.6, 2001, both John Wiley and Sons, Inc., N.Y.). In addition, methods and uses of the invention may be combined with other diagnostic methods to improve the outcome of the differential diagnosis. Other diagnostic methods such as PSA screening are well known.

The importance of accurately determining the presence or absence of prostatic cancer is evident. The impact on both the patient and health care system is further also evident. Thus, some embodiments of the methods and uses provide detecting of AMCAR, CK 5/6 and HMWCK within a given biological sample. The methods and uses comprises obtaining a biological sample from a subject, contacting said sample with the composition disclosed herein specific for the three proteins, detecting an interaction between the antibodies and the three proteins, wherein the detection of an interaction indicates the presence or absence of the three proteins, thereby allowing for e.g. detection of the three markers, detection of prostatic cancer, prostatic intraepithelial neoplasia (PIN), or benign mimics of prostate cancer in a biological sample, diagnosis, prognosis etc. according to any of the methods disclosed herein, the results of which one may determine if a subject is healthy, or is having prostate cancer.

PSA is the most common system used today for screening subjects and the PSA screening is known to have inherent problems giving false negatives or false positives. Specifically, subjects with PSA scores from 2-15, or more commonly 4-10 fall in a zone wherein measuring the PSA levels is not indicative of the presence of absence of disease.

The subjects falling within this gray zone are often falsely diagnosed as having or not having cancer. Subjects falling within this gray zone will benefit from the methods provided herein.

Within the disclosed methods and uses the three proteins AMCAR, CK 5/6 and HMWCK may be present at elevated levels, at decreased levels, or altogether absent within a sample taken from a subject in a particular clinical state (e.g., healthy or having prostate cancer).

Accordingly, differential presence of one or more of the three proteins found in a given biological sample provides useful information regarding a probability of whether a subject being tested has prostate cancer or is healthy. A probability that a subject being tested has prostate cancer or is healthy depends on whether the quantity of the three proteins in a test sample taken from said subject is statistically significant from a quantity the three proteins in a biological sample taken from healthy subjects or a control level known to exist in health subjects.

A difference in one of the three proteins found in a given biological sample may also be used to determine whether a subject known to have a prostate cancer is responding to a therapeutic treatment being administered. A quantity of the three proteins detected in a sample taken at time of therapy is compared to a quantity of the three proteins detected in a sample taken prior to an administration of treatment. In addition, a quantity of the three proteins detected in a sample taken at time of therapy is compared to a reference of the three proteins indicative of a healthy subject. Based on a comparison, one can determine whether said subject is responding to a therapeutic treatment, and to what degree the response is.

Furthermore, a difference in presence of the three proteins found in a given biological sample may also be used to determine whether a subject known to have a prostate cancer will respond to a given therapeutic treatment. A quantity of the three proteins detected in a sample taken from a subject diagnosed as having a prostate cancer is compared to reference panels of the three proteins taken from subjects with similar diagnoses that have undergone different forms of treatment. Reference panels of the three proteins generated from samples taken from subjects exposed to a given treatment, wherein the treatment resulted in a positive outcome are considered to indicate that the given treatment had a positive effect on the subject and therefore would be deemed successful. Reference panels of the three proteins generated from samples taken from subjects exposed to a given treatment, wherein the treatment resulted in a neutral outcome are considered to indicate that the given treatment had no therapeutic effect on the subject and would therefore be deemed unsuccessful. Reference panels of the three proteins generated from samples taken from subjects exposed to a given treatment, wherein the treatment resulted in a negative outcome are considered to indicate that the given treatment had no therapeutic effect on the subject and would be deemed unsuccessful. Based on the comparison, one skilled in the art would be able to administer the best mode of treatment for said subject.

Additionally, differential presence of the three proteins found in a given biological sample may also be used to determine the stage of prostate cancer in a subject.

A quantity of the three proteins detected in a sample taken from a subject diagnosed as having a prostate cancer is compared to reference biomarker panel taken from subjects known to have a specific stage or grade of prostate cancer. Based on the comparison, one would be able to determine the stage or grade at which the prostate cancer within said subject.

The three proteins AMCAR, CK 5/6 and HMWCK may be present at elevated levels, at decreased levels, or altogether absent within a sample taken from a subject in a particular clinical state (e.g., healthy or having prostate cancer).

Accordingly, presence of the three proteins found in a given biological sample provides useful information regarding a probability of whether a subject being tested has prostate cancer or is healthy. A probability that a subject being tested has prostate cancer or is healthy depends on whether the quantity of the three proteins in a test sample taken from said subject is statistically significant from a quantity of the three proteins in a biological sample taken from healthy subjects or a control level known to exist in health subjects.

A subject that is said to have prostate cancer possesses morphological, biochemical, and functional alterations of their prostate tissue such that the tissue can be characterized as a malignant neoplasm. The stage to which a prostate cancer has progressed can be determined using known methods currently available and presented herein. Currently, the most widely used method for determining the extent of malignancy of a prostate neoplasm is the Gleason Grading system. Gleason grading is based exclusively on the architectural pattern of the glands of a prostate neoplasm, wherein the ability of neoplastic cells to structure themselves into glands resembling those of the normal large intestine is evaluated using a scale of 1 to 5. For example, neoplastic cells that are able to architecturally structure themselves such that they resemble normal gland structure are graded 1-2, whereas neoplastic cells that are unable to do so are graded 4-5. A prostate neoplasm has tumor structure that is nearly normal will tend to behave, biologically, as normal tissue and therefore it is unlikely that it will be aggressively malignant.

A subject that is said to have non-malignant disease of the large intestine possesses morphological and/or biochemical alterations of their prostate tissue but does not exhibit malignant neoplastic properties. Such diseases include, but are not limited to, inflammatory and proliferative lesions, as well as benign disorders of the large intestine.

Data analysis to analyse the presence or absence of the three proteins AMCAR, CK 5/6, and HMWCK may include the steps of determining signal strength (e.g., intensity of peaks) of a biomarker(s) detected and removing "outliers" (data deviating from a predetermined statistical distribution). An example is the normalization of peaks, a process whereby the intensity of each peak relative to some reference is calculated. For example, a reference can be background noise generated by an instrument and/or a chemical (e.g., energy absorbing molecule), which is set as zero in the scale. Then the signal strength detected for each protein can be displayed in the form of relative intensities in the scale desired (e.g., 100). In an embodiment, an observed signal for a given peak can be expressed as a ratio of the intensity of that peak over the sum of the entire observed signal for both peaks and background noise in a specified mass to charge ratio range. In an embodiment, a standard may be admitted with a sample so that a peak from the standard can be used as a reference to calculate relative intensities of the signals observed for each proteins detected.

The resulting data can be transformed into various formats for displaying, typically through the use of computer algorithms. Using any of the above display formats, it can be readily determined from a signal display whether the three proteins are detected in a sample.

Exemplary method may be used to e.g. diagnosis, prognosis, staging of prostate cancer, predict treatment outcome, predict the likelihood of prostate cancer recurrence etc. as further described herein.

Recurrence means the prostate cancer has returned after an initial (or subsequent) treatment(s). Representative initial treatments include radiation treatment, chemotherapy, anti-hormone treatment and/or surgery (e.g., prostatectomy).

Some methods disclosed herein are useful for prostate cancer prognosis. Prognosis is the likely outcome of the disease (typically independent of treatment).

The methods disclosed herein may be used to prognose, i.e. to predict, prostate cancer likely outcome of the disease such as e.g. a recurrence in a sample collected well prior to such recurrence. A poor (or poorer) prognosis is likely for a subject with a more aggressive cancer.

In some method embodiments, a poor prognosis is less than 5 year survival (such as less than 1 year survival or less than 2 year survival) of the patient after initial diagnosis of the neoplastic disease. In some method embodiments, a good prognosis is greater than 2-year survival (such as greater than 3-year survival, greater than 5-year survival, or greater than 7-year survival) of the patient after initial diagnosis of the neoplastic disease.

Still other method embodiments predict treatment outcome in prostate cancer patients, and are useful for directing (e.g., selecting useful) treatment modalities for prostate cancer patients. As discussed elsewhere in this specification, expression of the disclosed proteins predicts that prostate cancer treatment (e.g., prostatectomy) is likely to fail (e.g., the disease will recur). Hence, the disclosed proteins can be used by caregivers to counsel prostate cancer patients as to the likely success of treatment (e.g., prostatectomy). Taken in the context of the particular subject's medical history, the patient and the caregiver can make better informed decisions of whether or not to treat (e.g., perform surgery, such as prostatectomy) and/or whether or not to provide alternate treatment (such as, external beam radiotherapy, brachytherapy, chemotherapy, or watchful waiting).

The present invention relates thus relates to methods for diagnosis and prognosis of prostate cancer by detecting the three proteins AMCAR, CK 5/6 and HMWCK expressed within a biological sample of a given subject, wherein the presence or absence of the three proteins allows for the diagnosis or prognosis of a subject as healthy or having prostate cancer. In one embodiment, the methods detect the presence of the three proteins in a sample wherein the marker is not expressed in healthy, disease-free individuals. In related embodiments, the methods of the invention detect elevated levels of the three proteins that are present at higher levels in samples from individuals that have cancer, e.g., prostate cancer, as compared to normal, healthy individuals.

A further aspect of the present invention is an in vitro method for detecting at least three different proteins in a biological sample, and wherein the at least three different proteins are AMCAR, CK 5/6, and HMWC, the method comprising the steps of
  a) contacting said sample with a composition comprising at least three primary antibodies or fragments thereof, wherein the at least three antibodies or fragments thereof binds specifically to at least three different proteins, and wherein the at least three different proteins are AMCAR, CK 5/6, and HMWC, for a sufficient time to form at least three antigen-antibody complexes,
  b) detecting said at least three antigen-antibody complexes,
  c) comparing the amount of antigen-antibody complexes detected to a positive and/or negative control, thereby detecting the at least three different proteins.

Optionally, a scoring may be done of the detected antigen-antibody complexes according to a standard scoring system known in the art or described herein.

The sample may, of course, be any biological sample which possibly may comprise the proteins AMCAR, CK 5/6, and HMWCK. Example of samples are tissue samples or cell samples from humans, rodents, such as mice, rats, guinea pigs, or from goats, sheeps, pigs, camles, dogs, cats, and even rabbits or otherwise as disclosed herein. In one embodiment, the sample is from a human.

In still a further embodiment, the sample is a tissue sample such as a human tissue sample.

The tissue samples needs to be prepared in order to work and pre-treatment of the tissue sample may be done. The tissue samples needs to be cut in appropriate sections, such as e.g. about 4 µm or appropriate to fit the method. The composition may be used on formalin-fixed, paraffin-embedded tissue sections. One example is pre-treatment with heat-induced epitope retrieval (HIER, Dako), or by pretreating tissues using EnVision™ FLEX Target Retrieval Solution, High pH (10×), (Dako Autostainer/Autostainer Plus). Further examples of antigen retrieval is Water bath methods using conventional methods know in the art, water bath methods using DAKO PT Link pri.dako.com/00091 demasking antigens us.pdf), pressure cocker heating, autoclave heating, microwave oven heating, proteolytic pre-treatment, combined proteolytic pre-treatment and HIER, combined deparaffinization and target retrieval.

One example of preparing de-parafinized sections is that sections may be deparaffinized by pre-treatment of deparaffinized formalin-fixed, paraffin-embedded tissue sections, e.g. by using Dako PT Link (Dako). Follow the pre-treatment procedure for EnVision™ FLEX Target Retrieval Solution, High pH (10×), (Dako Autostainer/Autostainer Plus) (Code K8014) the following parameters should be used for PT Link: Pre-heat temperature: 65° C.; epitope retrieval temperature and time: 97° C. for 20 (±1) minutes; cool down to 65° C. Remove Autostainer slide rack with slides from the PT Link tank and immediately dip slides into a jar/tank (e.g., PT Link Rinse Station, Code PT109) containing diluted room temperature EnVision™ FLEX Wash Buffer (10×), (Dako Autostainer/Autostainer Plus) (Code K8010). Leave slides in Wash Buffer for 1-5 minutes.

For paraffin-embedded sections, an aqueous mounting medium for coverslipping may be used (Dako Faramount Code S3025). As alternative specimen preparation, both deparaffinization and epitope retrieval may be performed in the PT Link using a modified procedure. After the staining procedure has been completed, the sections may be air dried at 60° C., immersed in xylene and mounted using permanent mounting medium. Alcohol should be avoided with permanent mounting as it may diminish reactivity of the red choromogen.

Before mounting, the tissue sections should not dry out during the pre-treatment or during the following immunohistochemical staining procedure.

In a further embodiment, the positive control comprises the at least three proteins. In a further embodiment, the positive control comprises prostate tissue.

In still a further embodiment, the negative control does not comprise the at least three proteins.

A further aspect is a method for detection in vitro of prostate cancer, or prostatic intraepithelial neoplasia (PIN), or benign mimics of prostate cancer in a biological sample in a biological sample, the method comprising the steps of
  a) contacting said sample with a composition comprising at least three primary antibodies or fragments thereof, wherein the at least three antibodies or fragments thereof binds specifically to at least three different proteins, and wherein the at least three different proteins are AMCAR, CK 5/6, and HMWC, for a sufficient time to form at least three different antigen-antibody complexes on the prostate cells,
  b) detecting said at least three antigen-antibody complexes,
  c) comparing the amount of antigen-antibody complexes to a positive and/or negative control,
  thereby detecting the prostate cancer, or prostatic intraepithelial neoplasia (PIN), or benign mimics of prostate cancer.

Optionally, a scoring may be done of the detected antigen-antibody complexes according to a standard scoring system known in the art or described herein.

The sample may be any sample possibly comprising prostate cancer, or prostatic intraepithelial neoplasia (PIN), or benign mimics of prostate cancer.

A further embodiment is wherein the positive control comprises cells from a subject who is suffering from the prostate cancer, or prostatic intraepithelial neoplasia (PIN), or benign mimics of prostate cancer.

A further embodiment is wherein the negative control comprises cells from healthy subjects who is not suffering from prostate cancer, or prostatic intraepithelial neoplasia (PIN), or benign mimics of prostate cancer.

A further embodiment is wherein the prostate cancer is any stage of prostate cancer as exemplified herein or known in the art of staging prostate cancer, such as e.g. Jewett-Withmore system, or TNM System.

A further aspect is a method for in vitro diagnosing and/or prognosing prostate cancer, or prostatic intraepithelial neoplasia (PIN), or benign mimics of prostate cancer in a biological sample, the method comprising the steps of
 a) contacting the sample with a composition comprising at least three primary antibodies or fragments thereof, wherein the at least three antibodies or fragments thereof binds specifically to at least three different proteins, and wherein the at least three different proteins are AMCAR, CK 5/6, and HMWC, for a sufficient time to form at least three different antigen-antibody complexes,
 b) detecting said at least three antigen-antibody complexes,
 c) comparing the amount of antigen-antibody complexes detected to a positive and/or negative control, thereby diagnosing and/or prognosing the prostate cancer, or prostatic intraepithelial neoplasia (PIN), or benign mimics of prostate cancer.

Optionally, a scoring may be done of the detected antigen-antibody complexes according to a standard scoring system known in the art or described herein.

The sample may be any sample possibly comprising prostate cancer, or prostatic intraepithelial neoplasia (PIN), or benign mimics of prostate cancer.

Further embodiments are wherein the positive control comprises cells from a subject who is suffering from the prostate cancer, or prostatic intraepithelial neoplasia (PIN), or benign mimics of prostate cancer.

Even further embodiments are wherein the negative control comprises cells from healthy subjects who is not suffering from prostate cancer, or prostatic intraepithelial neoplasia (PIN), or benign mimics of prostate cancer.

Still further embodiments are wherein the prostate cancer is selected from any stage of prostate cancer as exemplified herein or known in the art of staging prostate cancer, such as e.g. Jewett-Withmore system, or TNM System.

Thus, the method of diagnosis or prognosis of prostate cancer by detecting expression or not of the three proteins AMCAR, CK 5/6 and HMWCK within a biological sample of a given subject may be wherein the presence or absence of the three proteins allows for the diagnosis or prognosis of a subject as healthy or having prostate cancer. In one embodiment, the methods detect the presence of the three proteins in a sample wherein the marker is not expressed in healthy, disease-free individuals. In related embodiments, the methods of the invention detect elevated levels of the three proteins that are present at higher levels in samples from individuals that have cancer, e.g., prostate cancer, as compared to normal, healthy individuals. This is further visualized in the Examples disclosed herein.

In one embodiment, the method of diagnosis or prognosis of prostate cancer comprises: obtaining a biological sample from a given subject, contacting said sample with the composition disclosed herein under specific binding conditions, allowing the antibodies binding to AMCAR, CK 5/6, and HMWCK to bind to three proteins, detecting the antibodies using a detection method, wherein the detection method generates a profile of the expression of said three proteins within the sample, transforming the profile generated into a computer-readable form, and comparing the profile of said sample with a database containing profiles from comparable samples specific for healthy subjects, subjects having prostate cancer, and/or subjects having a non-malignant disease of the large intestine. The outcome of said comparison will allow for the determination of whether the subject from which the biological sample was obtained, is healthy or has prostate cancer based on the presence, absence or comparative quantity of the three proteins.

In further embodiments, the three proteins AMCAR, CK 5/6, HMW CK may be used in combination with another diagnostic tool to diagnose a subject as being healthy or having prostate cancer. For example, biomarker membrane metallo endopeptidase (MME) or gamma-glutamyltranspeptidase 1 (GGTI) may be used in combination with other diagnostic tools specific for prostate cancer detection such as, but not limited to, rectal palpitation, biopsy evaluation using Gleason scoring, radiography and symptomological evaluation by a qualified clinician or determination of PSA levels.

Physicians routinely use digital rectal examination (DRE) and assays for blood prostate-specific antigen (PSA) to screen men for prostatic cancer. If either or both tests are abnormal the doctors will order a biopsy to confirm their findings. The biopsy tissues are then examined by a pathologist. Prostate cancer can be confused with seminal vesicle, inflammatory and reactive conditions especially when tissues are limited and their morphology is similar. The composition of the present invention comprising antibodies binding specifically to the at least three different proteins AMCAR, CK 5/6, and HMWC is useful for detecting ambiguous lesions since antibodies binding to CK5/6 and HMWCK will detect basal cells and will score negative in ambiguous lesions. AMCAR will score positive for cancers and score negative for benign lesion. A process for the diagnosis of prostate cancer is illustrated in FIG. 4.

The amount of CK5/6, AMCAR and HMWCK in a sample may be determined using methods well known in the art. Suitable methods for assaying said protein (or antigen) levels in a biological sample include antibody-based techniques. For example, protein expression of the said proteins in tissues can be studied with classical immunohistological methods. In these, the specific recognition is provided by the primary antibody (polyclonal or monoclonal) in the composition according to the invention. A secondary detection system can utilize fluorescent, enzyme, or other conjugated secondary antibodies, as discussed herein. As a result, an immunohistological staining of tissue section for pathological examination is obtained.

In one embodiment, the biological samples to be tested are identified as samples associated with prostate cancer, prostatic intraepithelial neoplasia (PIN), or benign mimics of prostate cancer by the up- or down-regulation of the at least three proteins wherein the at least three different proteins are AMCAR, CK 5/6, and HMWC protein levels compared to corresponding normal healthy cells. By "upregulated" we mean that protein is increased by at least 10% compared to expression of the protein in normal (healthy) cells. Similarly, by "downregulated" we mean that protein is decreased by at least 10% compared to the expression of the protein in normal (healthy) cells. For example, the level of the proteins may be increased by at least 20%, 30%, 40%, 50%, or even 100% or more. Means to measure levels of antigens on cells are enclosed herein and further known in the art.

In a further embodiment, the above methods further comprise the step of detecting the location of the composition in the biological sample, i.e. tissue sample such as a human prostate tissue sample.

Detecting the compound or antibody can be achieved using methods well known in the art of clinical imaging and diagnostics further described herein and in the art. The specific method required will depend on the type of detectable label attached to the antibodies of the composition according to the invention.

A further aspect is an in vitro method for predicting outcome of treatment in a subject of prostatic cancer, or prostatic intraepithelial neoplasia (PIN), or benign mimics of prostate cancer patients, the method comprising the steps of
 a) detecting the expression of at least three different proteins, and wherein the at least three different proteins are AMCAR, CK 5/6, and HMWC,
 b) comparing the expression of said three proteins to a positive and/or negative control,
and thereby predicting the outcome of treatment of the prostate cancer, or prostatic intraepithelial neoplasia (PIN), or benign mimics of prostate cancer in said subject based on the detected expression of said three proteins.

Optionally, a scoring may be done of the detected antigen-antibody complexes according to a standard scoring system known in the art or described herein.

The sample may be any sample possibly comprising prostate cancer, or prostatic intraepithelial neoplasia (PIN), or benign mimics of prostate cancer, preferably a biological sample from a subject having prostatic cancer, or prostatic intraepithelial neoplasia (PIN), or benign mimics of prostate cancer.

A further aspect is an in vitro method of assessing efficacy of treatment of prostatic cancer, or prostatic intraepithelial neoplasia (PIN), or benign mimics of prostate cancer, the method comprising the steps of
 a) providing a biological sample from a subject having prostatic cancer, or prostatic intraepithelial neoplasia (PIN), or benign mimics of prostate cancer,
 b) detecting at least three different proteins, and wherein the at least three different proteins are AMCAR, CK 5/6, and HMWC,
 b) repeating step a) at one or more time points during treatment of said subject for prostatic cancer, or prostatic intraepithelial neoplasia (PIN), or benign mimics of prostate cancer,
and wherein a change in relative expression of the at least three proteins AMCAR, CK5/6 and HMWCK over time indicates effective treatment. Thus, an indication of effective treatment is a relative change in decreasing markers that identify malignant cells, i.e. an over time decrease in expression of AMCAR and increase over time in expression of CK5/6 and HMWCK relative a in time previous sample analysed in the steps of repeating the method.

Optionally, a scoring may be done of the detected antigen-antibody complexes according to a standard scoring system known in the art or described herein.

The sample may be any sample possibly comprising prostate cancer, or prostatic intraepithelial neoplasia (PIN), or benign mimics of prostate cancer, preferably a biological sample from a subject having prostatic cancer, or prostatic intraepithelial neoplasia (PIN), or benign mimics of prostate cancer, and that subject will be, is in-between or is currently under treatment.

A further aspect is an in vitro method of assessing recurrence of prostatic cancer, or prostatic intraepithelial neoplasia (PIN), or benign mimics of prostate cancer, the method comprising the steps of
 a) providing a biological sample from a subject having previously had prostatic cancer, or prostatic intraepithelial neoplasia (PIN), or benign mimics of prostate cancer,
 b) detecting at least three different proteins, and wherein the at least three different proteins are AMCAR, CK 5/6, and HMWC,
 b) repeating step a) at one or more time points during treatment of said subject for prostatic cancer, or prostatic intraepithelial neoplasia (PIN), or benign mimics of prostate cancer,
and wherein a change in relative expression of the at least three proteins AMCAR, CK5/6 and HMWCK over time indicates recurrence of prostatic cancer, or recurrence of prostatic intraepithelial neoplasia (PIN), or recurrence of benign mimics of prostate cancer. Thus, an indication of recurrence is a relative change in increasing markers that identify malignant cells, i.e. an over time increase in expression of AMCAR and a decrease over time in expression of CK5/6 and HMWCK relative a in time previous sample analysed in the steps of repeating the method.

The methods provided herein may be performed manually, or, preferably, on an automated staining device. Thus, in one embodiment the methods are performed manually.

In further embodiments, the methods are performed on an automated staining device.

In a further embodiment, the methods provided herein may be used in tissue micro arrays. Tissue micro arrays are also known and described in the art. Typically, tissue micro arrays may typically contain 50 to 500 tissues on a single slide.

Examples of automated staining devices useful according to the present invention are to include, but not limits to, Dako Autostainer (DakoCytomation), BioGenex 16000™ (Biogenex), Nemesis™ (BIOCARE), and NexES, Benchmark, Capilary gp stainer (Ventana systems). For example, and automated staining using the composition according to the invention on a Dako autostainer is exemplified further in Example 1 and 2. The sample is then ready for visualisation, detection, an optional scoring and further analysis.

Visualisation and detection may be performed by using reagents readily available in the art. Examples of useful detection and visualization reagents and systems are polymer detection systems such as EnVision™ DuoFLEX doublestain System, high pH, (DAKO).

Further embodiments are wherein the detection is made manually, such as by a pathologist or a medical doctor or anyone equally trained to manually view and detect proteins by immunological staining, such as immunohistochemical straining on prostate tissue.

In further embodiments, the detection is made by image analysis. Suitable image analysis devices useful according to the present invention are to include, but are not limited to ACIS® III (Dako).

Uses of the Composition

Further aspects of the present invention include uses of the composition provided herein.

A further aspect of the present invention is use of the composition provided herein to detect at least three different proteins, and wherein the at least three different proteins are AMCAR, CK 5/6, and HMWCK.

An further aspect of the present invention is use of the composition provided herein to detect prostate cancer or prostatic intraepithelial neoplasia (PIN), or benign mimics of prostate cancer.

A further aspect of the present invention is use of the composition to diagnose or prognose prostate cancer or prostatic intraepithelial neoplasia (PIN), or benign mimics of prostate cancer.

A further aspect of the present invention is use of the composition to predict outcome of treatment of prostate cancer or prostatic intraepithelial neoplasia (PIN), or benign mimics of prostate cancer.

A further aspect of the present invention is use of the composition to assess efficacy of treatment of prostate cancer or prostatic intraepithelial neoplasia (PIN), or benign mimics of prostate cancer.

A further aspect of the present invention is use of the composition to assess recurrence of prostate cancer or prostatic intraepithelial neoplasia (PIN), or benign mimics of prostate cancer.

Kits

The present invention also provides kits for immunoassays such as immunohistochemistry. Thus, a further aspect of the present invention provides a kit for immunoassays comprising a) the composition of the present invention provided herein and b) optionally, instructions for using the composition.

Further embodiments include visualisation reagents to be able to detect the composition binding specifically to the at least three different proteins AMCAR, CK 5/6, and HMWCK. Examples of visualisation and detection reagents are known in the art and given in e.g. (Antibodies: A Laboratory Manual, Harlow and Lane, Cold Spring Harbor Laboratory press, Cold Spring Harbor, N.Y. 1988, Current Protocols in Immunology, Unit 21.4, 2003, and Current Protocols in Molecular Biology, Unit 14.6, 2001, both John Wiley and Sons, Inc., N.Y.).

In some kit embodiments, the primary antibody can be directly labelled as described herein. Other kit embodiments will include secondary or further detection such as secondary antibodies (e.g., goat anti-rabbit antibodies, rabbit anti-mouse antibodies, anti-hapten antibodies) or non-antibody hapten-binding molecules (e.g., avidin or streptavidin) as described herein. In such kits, the secondary or further detection means may be directly labelled with a detectable moiety. In other instances, the secondary (or further) antibody or binding agent will be conjugated to a hapten (such as biotin, DNP, and/or FITC), which is detectable by a detectably labelled cognate hapten binding molecule (e.g., streptavidin (SA) horseradish peroxidase, SA alkaline phosphatase). Some kit embodiments may include colorimetric reagents (e.g., DAB, and/or AEC) in suitable containers to be used in concert with primary or secondary (or higher order) detection means (e.g., antibodies or binding entities) that are labelled with enzymes for the development of such colorimetric reagents.

In some embodiments, a kit includes positive or negative control samples, such as a cell line or tissue known to express or not express AMCAR, CK 5/6, and/or HMWCK. Examples of control samples include but are not limited to normal (e.g., non cancerous) cells or tissues, prostate cancer samples from subject known not to have or have had prostate cancer or prostate cancer recurrence following prostatectomy (e.g., at least 5 years or at least 10 years following prostatectomy). In some embodiments, a kit includes instructional materials disclosing, for example, means of use of the composition or further binding entities or detection means, e.g. an antibody, that specifically binds AMCAR, CK 5/6, and/or HMWCK or means of use for a particular reagent. The instructional materials may be written, in an electronic form (e.g., computer diskette or compact disk) or may be visual (e.g., video files). The kits may also include additional components to facilitate the particular application for which the kit is designed. Thus, for example, the kit can include buffers and other reagents routinely used for the practice of a particular disclosed method. Such kits and appropriate contents are well known to those of skill in the art.

The kit may further comprise, in an amount sufficient for at least one assay, the composition according to the invention as a separately packaged reagent.

Instructions for use of the packaged reagent are also typically included. Such instructions typically include a tangible expression describing reagent concentrations and/or at least one assay method parameter such as the relative amounts of reagent and sample to be mixed, maintenance time periods for reagent/sample admixtures, temperature, buffer conditions and the like.

An further aspect of the present invention provides a kit for detection of at least three different proteins in a biological sample in vitro, and wherein the at least three different proteins are AMCAR, CK 5/6, and HMWC, the kit comprising a) the composition provided herein, and b) instructions for using the composition.

A further aspect of the present invention provides a kit for detection of prostate cancer, or prostatic intraepithelial neoplasia (PIN), or benign mimics of prostate cancer in a biological sample in vitro, the kit comprising a) the composition provided herein, and b) instructions for using the composition.

A further aspect of the present invention provides a kit for diagnosing and/or prognosing prostate cancer, or prostatic intraepithelial neoplasia (PIN), or benign mimics of prostate cancer in a biological sample in vitro, the kit comprising a) the composition provided herein, and b) instructions for using the composition.

A further aspect of the present invention provides a kit for predicting outcome of treatment in a subject of prostatic cancer, or prostatic intraepithelial neoplasia (PIN), or benign mimics of prostate cancer patients, the kit comprising a) the composition provided herein, and b) instructions for using the composition.

A further aspect of the present invention provides a kit for assessing efficacy of treatment of prostatic cancer, or prostatic intraepithelial neoplasia (PIN), or benign mimics of prostate cancer, the kit comprising a) the composition provided herein, and b) instructions for using the composition.

A further aspect of the present invention provides a kit for assessing recurrence of prostatic cancer, or prostatic intraepithelial neoplasia (PIN), or benign mimics of prostate cancer, the kit comprising a) the composition provided herein, and b) instructions for using the composition.

Certain kit embodiments can include a carrier means, such as a box, a bag, a satchel, plastic carton (such as moulded plastic or other clear packaging), wrapper (such as, a sealed or sealable plastic, paper, or metallic wrapper), or other container.

In some examples, kit components will be enclosed in a single packaging unit, such as a box or other container, which packaging unit may have compartments into which one or more components of the kit can be placed. In other examples, a kit includes a one or more containers, for instance vials, tubes, and the like that can retain, for example, one or more biological samples to be tested.

Other kit embodiments include, for instance, syringes, cotton swabs, or latex gloves, which may be useful for handling, collecting and/or processing a biological sample. Kits may also optionally contain implements useful for moving a biological sample from one location to another, including, for example, droppers, syringes, and the like. Still other kit embodiments may include disposal means for discarding used or no longer needed items (such as subject samples, etc.). Such disposal means can include, without limitation, containers that are capable of containing leakage from discarded materials, such as plastic, metal or other impermeable bags, boxes or containers.

Non-limiting examples which embody certain aspects of the invention will now be described.

EXAMPLES

Example 1

A Staining Protocol Using a Composition According to the Invention

Material and Methods

Tissues used are sample biopsies from subjects known with prostatic cancer lesions, suspected to have prostatic lesions and healthy subjects.

1. Deparaffinization: Histoclear 5'×2, 100% Alcohol 3'×2, 95% Alcohol 3'×2, DiH2O bath.
2. Pre-treatment (Target Retrieval Solution High pH DM812, DAKO) (20 minutes at 97° C. in the PT Module)
3. Wash buffer (TBST, S3006, DAKO), rinse once
4. Dual enzyme block (DEEB, DAKO) S2003, 200-300 µL, 5 minutes
5. Wash buffer (TBST, S3006, DAKO), rinse once
6. Prostate cocktailed antibodies (P504s/HMWCK/CK5/6), 200-300 µL, 20 minutes.
7. Wash buffer (TBST, S3006, DAKO), rinse once
8. Link-HRP (cocktail of Swine anti Mouse Dextran-HRP and Goat anti-rabbit Dextran, DAKO). 200-300 µL, 20 minutes
9. Wash buffer (TBST, S3006, DAKO), rinse once
10. AP-enzyme (Rabbit anti-goat Dextran-AP, DAKO), 200-300 µL, 20 minutes
11. Wash buffer (TBST, S3006, DAKO), rinse twice.
12. DAB+, 200-300 µL, 10 minutes
13. Wash buffer (TBST, S3006, DAKO), rinse once
14. LPR (K0640, DAKO), 200-300 µL, 10 minutes
15. Wash buffer (TBST, S3006, DAKO), rinse once
16. Hematoxylin (DAKO), 200-300 µL, 5 minutes
17. Deionized water, rinse FIG. 3 provides an overview of the composition according to the invention and a detection system.

Example 2

Detection of AMCAR, CK 5/6, and HMWC in Prostate Tissue

Material and Methods
As in example 1.
Results

TABLE 1

Comparison for prostate basal markers and their combination (Mean ± SEM, n = 8)*

| Antibodies | Intensity | Score | Positive Basal Cell Area ($10^3 \mu M^2$) |
|---|---|---|---|
| 34βE12 | 121 ± 4.63 | 2.92 ± 0.16 | 1344.29 ± 291.66 |
| 34βE12/CK5/6 | 120 ± 3.74 | 2.88 ± 0.13 | 1744.80 ± 347.36 |
| 34βE12/P63 | 124 ± 3.80 | 3.02 ± 0.13 | 1768.63 ± 308.79 |
| CK5/6 | 112 ± 4.36 | 2.60 ± 0.15 | 1099.89 ± 244.30 |
| P63 | 83 ± 4.77 | 1.59 ± 0.21 | 372.81 ± 108.35 |

The stained slides were scanned and analyzed objectively with a Dako ACIS III image system.

All data (intensity, score, and positive basal cell area) in Table 1 are measured using ACIS III software. Statistics was performed with statistic software Minitab 15.

Figure 1:
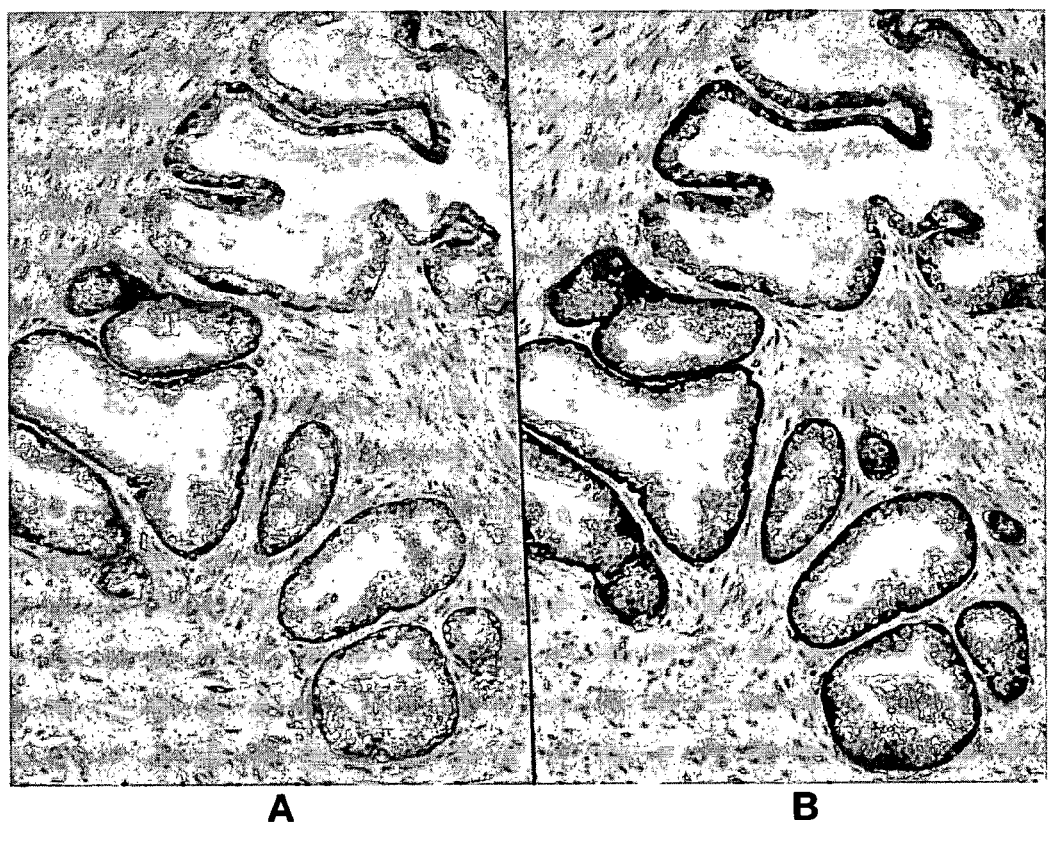
FIG. 1 shows IHC staining using a composition comprising antibodies binding to AMCAR/HMWCK (A), a composition comprising antibodies binding to AMCAR/HMWCK/CK5/6 (B).
Figure 2:
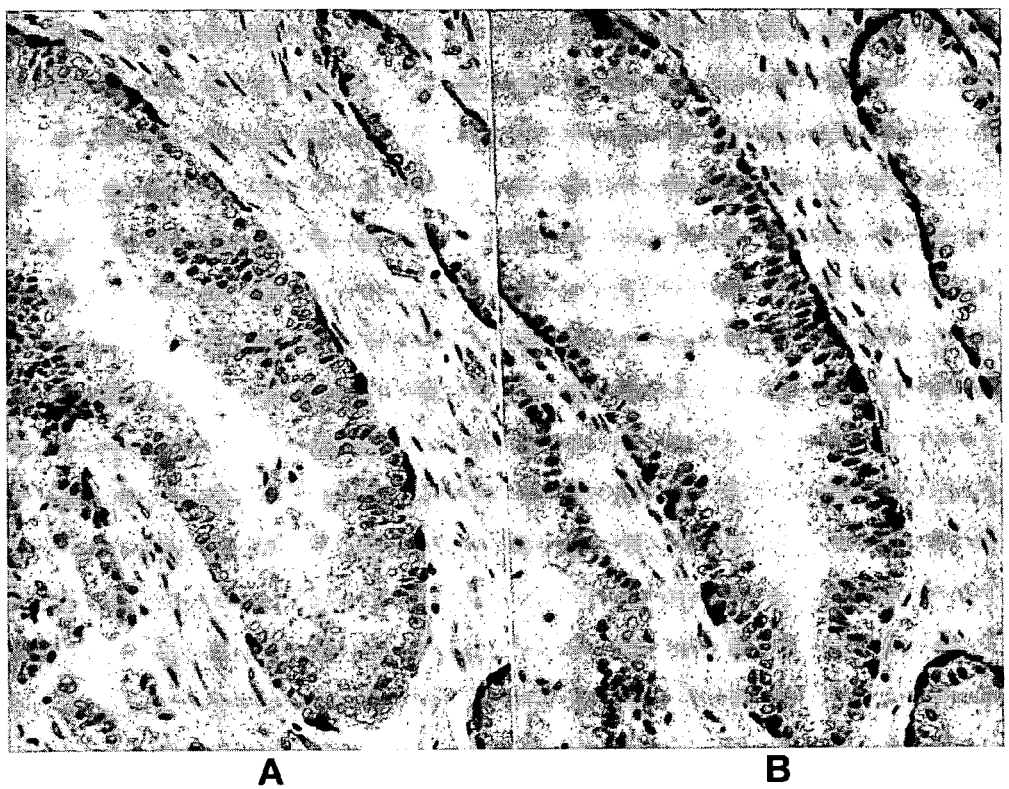
FIG. 2 shows IHC staining using antibodies binding to AMCAR/HMWCK/p63 (PIN4, BioCare) (A) and a composition according to the invention comprising antibodies binding respectively to AMCAR, HMWCK (clone 34βE12), and CK5/6 (B).

FIG. 1 shows IHC staining using a composition comprising antibodies binding to P504s/34βE12 (A) and a composition comprising antibodies binding to P504s/34βE12/CK5/6 (B). Improved IHC staining is seen in the normal prostate and hyperplastic glands using the three-antibody cocktail (B) as compared to the two-antibody cocktail (A).

Positive stained areas for 34βE12, 34βE12/CK5/6, and 34βE12/p63 are significantly higher than p63 stained area. There are no significant differences for staining intensity, score and positive area between 34βE12/CK5/6 and 34βE12/p63 with 95% confidence interval. However, detection of positive basal cells using P504s/34βE12/CK5/6 cocktail are superior to P504s/34βE12/P63 (see FIG. 2) where more basal cells are stained in this areas when p504s/34βE12/CK5/6 is used (B in FIG. 2).

The cocktail (P504s/34βE12/CK5/6) also improves both the sensitivity and specificity of detecting prostate cancer from 98% to 100%, and from 89% to 100% respectively when compared to H&E (Table 2).

The H&E slides (30 cases, 21 prostatic hyperplasia and 9 adenocarcinoma cases) were reviewed by at least three pathologists. One false positive and one false negative were identified after we reviewed the P504s/34βE12/CK5/6 cocktail. If these cases were reviewed by less experienced pathologists, the false positive and false negative cased would be higher.

The new cases of prostate cancer in 2008 are about 186,320 in the US alone. This means 3,726 US patients would be misdiagnosed each year if further test such as the prostate cocktail is not used.

TABLE 2

Sensitivity and specificity of P504s/34βE12/CK5/6 cocktail and H&E (Sample size = 30, 21)

| | Sensitivity | Specificity |
|---|---|---|
| H&E | 98% | 89% |
| IHC Cocktail | 100% | 100% |

Conclusions

The present example provides an example of detection of AMCAR, CK 5/6, and HMWC in prostate tissue using the composition according to the invention as well as a comparison with existing reagents.

The cocktail (P504s/34βE12/CK5/6) also improves both the sensitivity and specificity of detecting prostate cancer from 98% to 100%, and from 89% to 100% respectively when compared to H&E Example 3

Detection of Prostate Cancer, or Prostatic Intraepithelial Neoplasia (PIN), or Benign Mimics of Prostate Cancer in a Biological Sample in Vitro Material and Methods
As in Example 1-2.
Results
FIGS. 5, 6 and 7 shows the results of stainings.
FIG. 5 shows the results of immunohistochemistry (IHC) stainings using an antibody cocktail of the invention comprising antibodies binding to P504s, HMWCK (clone 34βE12) and CK5/6 (A) compared to another antibody cocktail (PIN4, BioCare) comprising antibodies binding to P504s, CK5, CK14 and p63. More cells and stronger staining in the basal cell layer of the hyperplastic glands are seen in panel A compared to B. Arrows are pointing at the basal cell area showing fewer basal cells stained in panel B, compared to stained basal cells in panel A.

FIG. 6 shows the results of immunohistochemistry (IHC) stainings using an antibody cocktail of the invention comprising antibodies binding to P504s, HMWCK (clone 34βE12) and CK5/6 (A) compared to another antibody cocktail (PIN4, BioCare) comprising antibodies binding to P504s, CK5, CK14 and p63. More cells and stronger staining in the basal cell layer of the athrophy glands are seen in panel A compared to B.

FIG. 7 shows the results of immunohistochemistry (IHC) stainings using an antibody cocktail of the invention comprising antibodies binding to P504s, HMWCK (clone 34βE12) and CK5/6 (A) compared to another antibody cocktail (PIN4, BioCare) comprising antibodies binding to P504s, CK5, CK14 and p63. More cells and stronger staining in the basal cell layer of the prostatic intraepithelial neoplasia (PIN) and athrophy gland are seen in panel A compared to B. Cancerous glands are lack of basal cells (arrow).

Conclusions

The composition of the invention readily detects prostate cancer, or prostatic intraepithelial neoplasia (PIN), or benign mimics of prostate cancer in a superior way than antibody cocktails available, e.g. PIN4 (BioCare).

The invention claimed is:

1. A composition for detecting three different proteins, AMCAR, CK 5/6, and HMWCK, comprising three different primary antibodies or antigen-binding fragments thereof that bind specifically to the three different proteins, respectively, wherein the antibody recognizing AMCAR is an antibody produced by a rabbit clone 13H4 or an antigen-binding fragment thereof, wherein the antibody recognizing CK 5/6 is an antibody produced by a mouse clone D5/16 B4 or an antigen-binding fragment thereof, and wherein the antibody recognizing HMWCK is an antibody produced by a mouse clone 34βE12 or an antigen-binding fragment thereof, and wherein no additional primary antibodies or antigen-binding fragments thereof are present in the composition.

2. The composition according to claim 1, wherein at least one of the primary antibodies is a recombinant antibody.

3. The composition according to claim 1, further comprising a buffer.

4. A kit comprising:
 a. the composition of claim 1, and
 b. optionally, instructions for using the composition.

5. A method for in vitro detecting three different proteins in a biological sample, wherein the three different proteins are AMCAR, CK 5/6, and HMWCK, the method comprising the steps of
 a. contacting said sample with the composition of claim 1 for a sufficient time to form three different antigen-antibody complexes, and
 b. detecting said three different antigen-antibody complexes.

6. The method according to claim 5, further comprising a step of optionally scoring the amount of antigen-antibody complexes.

7. The method according to claim 5, further comprising step d) comparing the expression of said three proteins to at least one of a positive control and a negative control.

8. The method according to claim 5, which is performed on an automated staining device.

9. The method according to claim 5, wherein the detection is made manually.

10. The method according to claim 5, wherein the detection is made by image analysis.

11. The method according to claim 5, wherein the positive control comprises cells from a subject who is suffering from the prostate cancer, prostatic intraepithelial neoplasia (PIN), or benign mimics of prostate cancer.

12. The method according to claim 5, wherein the negative control comprises cells from a healthy subject who is not suffering from prostate cancer, prostatic intraepithelial neoplasia (PIN), or benign mimics of prostate cancer.

13. The method of claim 7, wherein the positive control comprises the proteins AMCAR, CK 5/6, and HMWCK.

14. The method of claim 7, wherein the negative control does not comprise the proteins AMCAR, CK 5/6, or HMWCK.

15. The method of claim 5, wherein the sample is obtained from a human prostate tissue sample.

16. The method of claim 15, wherein the prostate tissue sample is obtained from a subject that has, is suspected of having, or previously had prostate cancer, prostatic intraepithelial neoplasia (PIN), or benign mimics of prostate cancer.

17. A method for producing an antibody-labeled prostate sample, comprising:
 (i) providing a biological sample obtained from a sample of prostate tissue obtained from subject, and
 (ii) contacting the biological sample with the composition of claim 1;
 wherein the antibodies or antigen-binding fragments thereof bind to the sample to produce an antibody-labeled prostate sample.

18. The method of claim 17, further comprising detecting the bound antibodies or antigen-binding fragments thereof.

* * * * *